US012640248B2

(12) United States Patent
Ryoo et al.

(10) Patent No.: US 12,640,248 B2
(45) Date of Patent: May 26, 2026

(54) MEDICINE PREPARATION ASSISTANCE DEVICE, METHOD FOR OPERATING SAME, AND APPLICATION

(71) Applicants: Ji Eun Ryoo, Suwon-si (KR); Soyeun Kang, Seoul (KR)

(72) Inventors: Ji Eun Ryoo, Suwon-si (KR); Soyeun Kang, Seoul (KR)

( * ) Notice: Subject to any disclaimer, the term of this patent is extended or adjusted under 35 U.S.C. 154(b) by 0 days.

(21) Appl. No.: 19/111,450

(22) PCT Filed: Nov. 28, 2023

(86) PCT No.: PCT/KR2023/019289
§ 371 (c)(1),
(2) Date: Mar. 13, 2025

(87) PCT Pub. No.: WO2024/204947
PCT Pub. Date: Oct. 3, 2024

(65) Prior Publication Data
US 2026/0011424 A1 Jan. 8, 2026

(30) Foreign Application Priority Data

Mar. 24, 2023 (KR) ........................ 10-2023-0038516
Oct. 12, 2023 (KR) ........................ 10-2023-0135905

(51) Int. Cl.
| | |
|---|---|
| *G16H 20/10* | (2018.01) |
| *G06V 30/19* | (2022.01) |
| *G16H 10/60* | (2018.01) |
| *G16H 30/20* | (2018.01) |

(Continued)

(52) U.S. Cl.
CPC ....... *G16H 20/10* (2018.01); *G06V 30/19007* (2022.01); *G16H 10/60* (2018.01); *G16H 30/20* (2018.01); *G16H 40/20* (2018.01); *G16H 70/40* (2018.01)

(58) Field of Classification Search
CPC ........ G16H 20/10; G16H 40/20; G16H 10/60; G16H 30/20; G16H 70/40; G06V 30/19007
See application file for complete search history.

(56) References Cited

U.S. PATENT DOCUMENTS

| | | | | |
|---|---|---|---|---|
| 7,567,707 B2 * | 7/2009 | Willamowski | ....... | G06V 40/193 |
| | | | | 358/518 |
| 7,764,846 B2 * | 7/2010 | Marchesotti | ......... | G06V 40/193 |
| | | | | 382/254 |

(Continued)

FOREIGN PATENT DOCUMENTS

| | | |
|---|---|---|
| JP | 05189464 A | 7/1993 |
| JP | 2016071624 A | 5/2016 |

(Continued)

OTHER PUBLICATIONS

Atitallah, Elsevier, 2020, pp. 1-29.*
Nguyen, Springer, 2022 pp. 344-369.*

*Primary Examiner* — Michael I Ezewoko
(74) *Attorney, Agent, or Firm* — Boyle Fredrickson, S.C.

(57) ABSTRACT

An electronic device according to one embodiment may, on the basis of photographing a prescription, obtain prescription information. The electronic device may, on the basis of photographing a medicine, determine whether the medicine matches the prescription information.

12 Claims, 10 Drawing Sheets

(51) Int. Cl.
    *G16H 40/20*         (2018.01)
    *G16H 70/40*         (2018.01)

(56)           References Cited

U.S. PATENT DOCUMENTS

| | | | | |
|---|---|---|---|---|
| 7,860,283 | B2 * | 12/2010 | Begelman | G06T 7/11 |
| | | | | 600/407 |
| 8,413,905 | B2 * | 4/2013 | Pourfallah | G07F 17/0014 |
| | | | | 235/492 |
| 8,477,989 | B2 * | 7/2013 | Bresolin | G01N 21/9508 |
| | | | | 382/142 |
| 8,908,163 | B2 * | 12/2014 | Young | G01N 21/31 |
| | | | | 356/72 |
| 9,290,010 | B2 * | 3/2016 | Hanina | H04N 19/99 |
| 9,400,909 | B2 * | 7/2016 | Hanina | G06V 20/66 |
| 9,406,142 | B2 * | 8/2016 | Gorman, III | G06T 7/174 |
| 9,495,752 | B2 * | 11/2016 | Wu | G06T 7/143 |
| 9,569,650 | B2 * | 2/2017 | Hanina | G06T 7/48 |
| 9,569,736 | B1 * | 2/2017 | Ghesu | G06N 3/084 |
| 9,697,335 | B2 * | 7/2017 | Joplin | G16H 20/10 |
| 9,700,219 | B2 * | 7/2017 | Sharma | A61B 6/507 |
| 9,707,400 | B2 * | 7/2017 | Grenz | A61N 1/368 |
| 9,792,531 | B2 * | 10/2017 | Georgescu | G06F 18/2413 |
| 9,904,992 | B2 * | 2/2018 | Takamori | G06T 7/0004 |
| 9,940,439 | B2 * | 4/2018 | Royaee | G16Z 99/00 |
| 9,968,257 | B1 * | 5/2018 | Burt | A61B 5/0035 |
| 9,978,139 | B2 * | 5/2018 | Kriheli | G16Z 99/00 |
| 10,192,129 | B2 * | 1/2019 | Price | G06N 3/0464 |
| 10,265,243 | B2 * | 4/2019 | Trower | B65D 75/54 |
| 10,311,302 | B2 * | 6/2019 | Kottenstette | G06V 10/82 |
| 10,366,288 | B1 * | 7/2019 | Kottenstette | G06V 10/451 |
| 10,373,313 | B2 * | 8/2019 | Ghesu | G06T 7/0012 |
| 10,521,902 | B2 * | 12/2019 | Avendi | G06T 3/02 |
| 10,593,033 | B2 * | 3/2020 | Niculescu-Mizil | G06T 11/008 |
| 10,600,184 | B2 * | 3/2020 | Golden | G06N 3/0985 |
| 10,643,072 | B2 * | 5/2020 | Kottenstette | G06F 18/2413 |
| 10,733,722 | B2 * | 8/2020 | Niculescu-Mizil | G16H 50/70 |
| 10,777,310 | B2 * | 9/2020 | Joplin | G07F 17/0092 |
| 10,835,761 | B2 * | 11/2020 | Bériault | G06N 3/0475 |
| 10,839,506 | B1 * | 11/2020 | Raghu | G06V 10/44 |
| 10,842,445 | B2 * | 11/2020 | Wang | G06T 7/35 |
| 10,853,937 | B2 * | 12/2020 | Niculescu-Mizil | |
| | | | | G06V 10/454 |
| 10,871,536 | B2 * | 12/2020 | Golden | G06N 3/0985 |
| 10,891,511 | B1 * | 1/2021 | Jiang | G06V 10/758 |
| 10,902,598 | B2 * | 1/2021 | Golden | G06N 3/084 |
| 10,943,163 | B2 * | 3/2021 | Moshkovitz | G06K 19/07354 |
| 10,967,202 | B2 * | 4/2021 | Van Heteren | A61N 5/1081 |
| 10,998,094 | B1 * | 5/2021 | Chiu | G16H 20/13 |
| 11,042,968 | B2 * | 6/2021 | Xu | G06N 3/08 |
| 11,083,913 | B2 * | 8/2021 | Lachaine | G16H 30/20 |
| 11,116,720 | B2 * | 9/2021 | Reddy | A61K 9/0031 |
| 11,151,378 | B2 * | 10/2021 | Kottenstette | G06V 10/764 |
| 11,176,670 | B2 * | 11/2021 | Lee | G06T 7/50 |
| 11,182,896 | B2 * | 11/2021 | Avendi | G06V 10/764 |
| 11,195,605 | B2 * | 12/2021 | Lamoncha | G16H 20/10 |
| 11,328,402 | B2 * | 5/2022 | Tang | G06T 7/0002 |
| 11,386,987 | B2 * | 7/2022 | Lamoncha | G06F 21/32 |
| 11,394,927 | B2 * | 7/2022 | Buibas | G01S 15/08 |
| 11,430,167 | B2 * | 8/2022 | Zhang | G06T 5/50 |
| 11,436,484 | B2 * | 9/2022 | Farabet | G06N 3/045 |
| 11,491,348 | B2 * | 11/2022 | Bériault | G06T 7/20 |
| 11,547,874 | B2 * | 1/2023 | Lachaine | G16H 30/20 |
| 11,551,353 | B2 * | 1/2023 | Golden | G06N 3/09 |
| 11,551,394 | B2 * | 1/2023 | Biswas | G06N 3/0464 |
| 11,557,036 | B2 * | 1/2023 | Liao | G06T 7/30 |
| 11,568,639 | B2 * | 1/2023 | Kottenstette | G06V 20/176 |
| 11,581,087 | B2 * | 2/2023 | Rusko | G06T 7/0012 |
| 11,651,487 | B2 * | 5/2023 | Arafati | G06N 3/0464 |
| | | | | 382/128 |
| 11,676,007 | B2 * | 6/2023 | Lovell | G05B 19/4207 |
| | | | | 706/25 |
| 11,676,247 | B2 * | 6/2023 | Zimmer | G06N 3/0455 |
| | | | | 382/299 |
| 11,741,605 | B2 * | 8/2023 | Liao | G06T 7/0012 |

| | | | | |
|---|---|---|---|---|
| 11,783,627 | B2 * | 10/2023 | Dagdeviren | G06V 40/174 |
| | | | | 382/103 |
| 11,789,453 | B2 * | 10/2023 | Chowdhary | G06T 7/62 |
| | | | | 382/110 |
| 11,843,624 | B1 * | 12/2023 | Estep | G06N 3/09 |
| 11,922,320 | B2 * | 3/2024 | Jaipuria | G06N 3/084 |
| 11,940,519 | B2 * | 3/2024 | O'Brien | G06V 10/774 |
| 11,947,682 | B2 * | 4/2024 | Zhang | H04L 63/1425 |
| 11,954,886 | B2 * | 4/2024 | Taamazyan | G06V 10/147 |
| 11,966,673 | B2 * | 4/2024 | Kristensen | G06N 3/088 |
| 11,996,186 | B2 * | 5/2024 | Lamoncha | G06Q 20/102 |
| 12,136,220 | B2 * | 11/2024 | Vasilev | G06N 3/0464 |
| 12,278,007 | B2 * | 4/2025 | Himeno | G16H 70/60 |
| 12,282,856 | B2 * | 4/2025 | Zhang | G06F 18/2413 |
| 12,283,046 | B2 * | 4/2025 | Min | A61B 6/032 |
| 12,299,885 | B2 * | 5/2025 | Min | A61B 5/055 |
| 12,324,695 | B2 * | 6/2025 | Min | A61B 5/7267 |
| 12,324,696 | B2 * | 6/2025 | Min | G16H 50/30 |
| 12,340,569 | B2 * | 6/2025 | Yoo | G06N 3/0464 |
| 12,380,560 | B2 * | 8/2025 | Min | G06T 7/0014 |
| 12,396,695 | B2 * | 8/2025 | Min | A61B 5/02007 |
| 12,406,365 | B2 * | 9/2025 | Min | A61B 5/7275 |
| 12,440,180 | B2 * | 10/2025 | Min | G06V 10/22 |
| 2007/0168221 | A1 * | 7/2007 | Blotter | G06Q 10/08 |
| | | | | 600/300 |
| 2008/0288287 | A1 * | 11/2008 | Stanners | G06Q 10/10 |
| | | | | 705/2 |
| 2009/0012820 | A1 * | 1/2009 | Bishop | G06Q 10/087 |
| | | | | 705/3 |
| 2010/0158332 | A1 * | 6/2010 | Rico | G06T 7/0012 |
| | | | | 382/128 |
| 2014/0086465 | A1 * | 3/2014 | Wu | G06T 7/11 |
| | | | | 382/131 |
| 2014/0236616 | A1 * | 8/2014 | Oberfest | G16H 40/67 |
| | | | | 705/2 |
| 2014/0236617 | A1 * | 8/2014 | Oberfest | G16H 20/10 |
| | | | | 705/2 |
| 2015/0178938 | A1 * | 6/2015 | Gorman, III | G06T 7/174 |
| | | | | 382/131 |
| 2016/0104277 | A1 * | 4/2016 | Takamori | G06T 7/0004 |
| | | | | 382/128 |
| 2017/0076059 | A1 * | 3/2017 | Morefield | G16H 50/30 |
| 2017/0109881 | A1 * | 4/2017 | Avendi | G06V 10/764 |
| 2017/0116497 | A1 * | 4/2017 | Georgescu | G16H 50/20 |
| 2017/0140236 | A1 * | 5/2017 | Price | G06N 3/08 |
| 2018/0260793 | A1 * | 9/2018 | Li | G06T 19/20 |
| 2018/0293552 | A1 * | 10/2018 | Zhang | G06Q 10/06313 |
| 2018/0315193 | A1 * | 11/2018 | Paschalakis | G06V 40/197 |
| 2018/0374204 | A1 * | 12/2018 | Manhart | G06T 3/14 |
| 2018/0374207 | A1 * | 12/2018 | Niculescu-Mizil | G06T 7/0004 |
| 2018/0374569 | A1 * | 12/2018 | Niculescu-Mizil | G06T 7/0008 |
| 2019/0156475 | A1 * | 5/2019 | Markson | G06T 7/70 |
| 2019/0244337 | A1 * | 8/2019 | Niculescu-Mizil | G06F 18/214 |
| 2019/0303759 | A1 * | 10/2019 | Farabet | G06F 9/455 |
| 2020/0111204 | A1 * | 4/2020 | Cosatto | G06F 18/211 |
| 2020/0380679 | A1 * | 12/2020 | Lee | G06T 7/0014 |
| 2020/0410687 | A1 * | 12/2020 | Siemionow | G06N 3/045 |
| 2021/0065861 | A1 * | 3/2021 | Lamoncha | G16H 20/10 |
| 2021/0065864 | A1 * | 3/2021 | Lamoncha | G16H 70/40 |
| 2021/0125707 | A1 * | 4/2021 | Rusko | G06T 7/11 |
| 2021/0158041 | A1 * | 5/2021 | Chowdhary | G06V 20/188 |
| 2021/0233273 | A1 * | 7/2021 | Spurr | G06F 18/217 |
| 2021/0286923 | A1 * | 9/2021 | Kristensen | G06N 3/096 |
| 2021/0294944 | A1 * | 9/2021 | Nassar | G05D 1/0088 |
| 2021/0339046 | A1 * | 11/2021 | Lachaine | A61N 5/1039 |
| 2021/0357555 | A1 * | 11/2021 | Liu | G06F 30/20 |
| 2022/0028085 | A1 * | 1/2022 | Vasilev | G06N 3/08 |
| 2022/0066544 | A1 * | 3/2022 | Kwon | G06T 7/251 |
| 2022/0084270 | A1 * | 3/2022 | Zhang | G06N 3/094 |
| 2022/0198617 | A1 * | 6/2022 | Gafni | G06N 20/00 |
| 2022/0198784 | A1 * | 6/2022 | Toporek | G06N 3/08 |
| 2023/0004801 | A1 * | 1/2023 | Farabet | G06N 3/082 |
| 2023/0005609 | A1 * | 1/2023 | Lamoncha | G06Q 20/102 |
| 2023/0106383 | A1 * | 4/2023 | Yao | G06T 3/4046 |
| | | | | 382/299 |
| 2023/0106440 | A1 * | 4/2023 | Golden | G06N 3/09 |
| | | | | 382/131 |

(56)　　　　　　　References Cited

U.S. PATENT DOCUMENTS

| | | | |
|---|---|---|---|
| 2023/0126829 A1* | 4/2023 | Grigorev | G06T 17/20 |
| | | | 345/419 |
| 2023/0154181 A1* | 5/2023 | Lorenzen | G06V 10/764 |
| | | | 382/103 |
| 2023/0197233 A1* | 6/2023 | Davey | G16H 10/60 |
| | | | 700/215 |
| 2023/0289596 A1* | 9/2023 | Lovell | G05B 19/4097 |
| 2023/0368383 A1* | 11/2023 | Liao | G06T 7/0012 |
| 2024/0012912 A1* | 1/2024 | Zhang | H04L 41/16 |
| 2024/0013067 A1* | 1/2024 | Azarafrooz | G06F 21/602 |
| 2024/0029415 A1* | 1/2024 | Shanbhag | G06V 10/774 |
| 2024/0047034 A1* | 2/2024 | Davey | G16H 20/10 |
| 2024/0061440 A1* | 2/2024 | Chowdhary | G06T 7/194 |
| 2024/0078363 A1* | 3/2024 | Nassar | G05D 1/0088 |
| 2024/0087130 A1* | 3/2024 | Siemionow | G06N 3/0475 |
| 2024/0092390 A1* | 3/2024 | Philion | G06N 3/006 |
| 2024/0161479 A1* | 5/2024 | Tyan | G06V 10/42 |
| 2025/0029713 A1* | 1/2025 | Lamoncha | G16H 70/40 |
| 2025/0061581 A1* | 2/2025 | Vasilev | G16H 30/40 |
| 2025/0166772 A1* | 5/2025 | Lamoncha | G16H 20/10 |

FOREIGN PATENT DOCUMENTS

| | | | |
|---|---|---|---|
| JP | 2021029450 A | 3/2021 | |
| JP | 2012164331 A | 8/2021 | |
| KR | 20120009662 A | 2/2012 | |
| KR | 20160097611 A | 8/2016 | |
| KR | 20190019079 A | 2/2019 | |
| KR | 20220067370 A | 5/2022 | |
| KR | 20230033782 A | 3/2023 | |

* cited by examiner

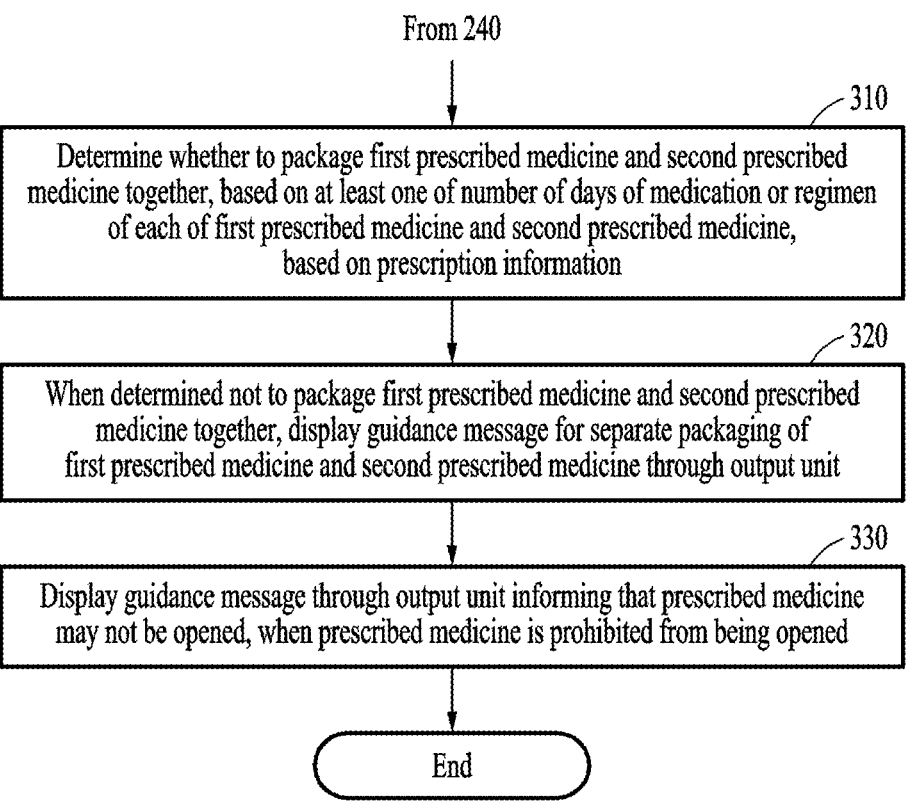

From 240

310

Determine whether to package first prescribed medicine and second prescribed medicine together, based on at least one of number of days of medication or regimen of each of first prescribed medicine and second prescribed medicine, based on prescription information

320

When determined not to package first prescribed medicine and second prescribed medicine together, display guidance message for separate packaging of first prescribed medicine and second prescribed medicine through output unit

330

Display guidance message through output unit informing that prescribed medicine may not be opened, when prescribed medicine is prohibited from being opened End

FIG. 3

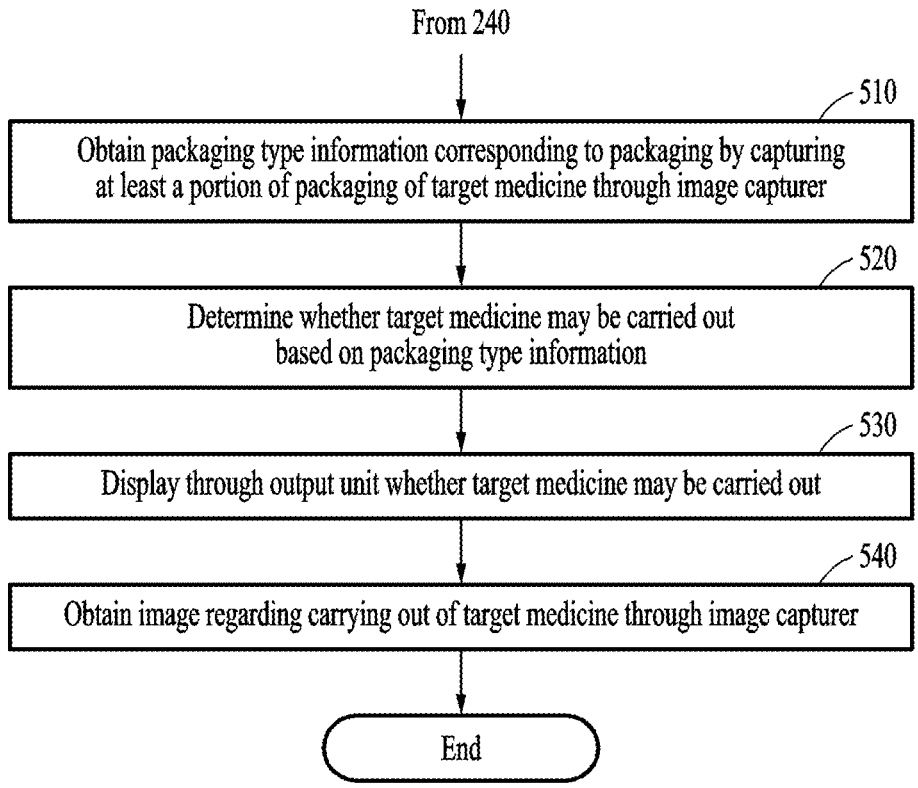

From 240

510
Obtain packaging type information corresponding to packaging by capturing at least a portion of packaging of target medicine through image capturer 520
Determine whether target medicine may be carried out based on packaging type information 530
Display through output unit whether target medicine may be carried out 540
Obtain image regarding carrying out of target medicine through image capturer End

FIG. 5

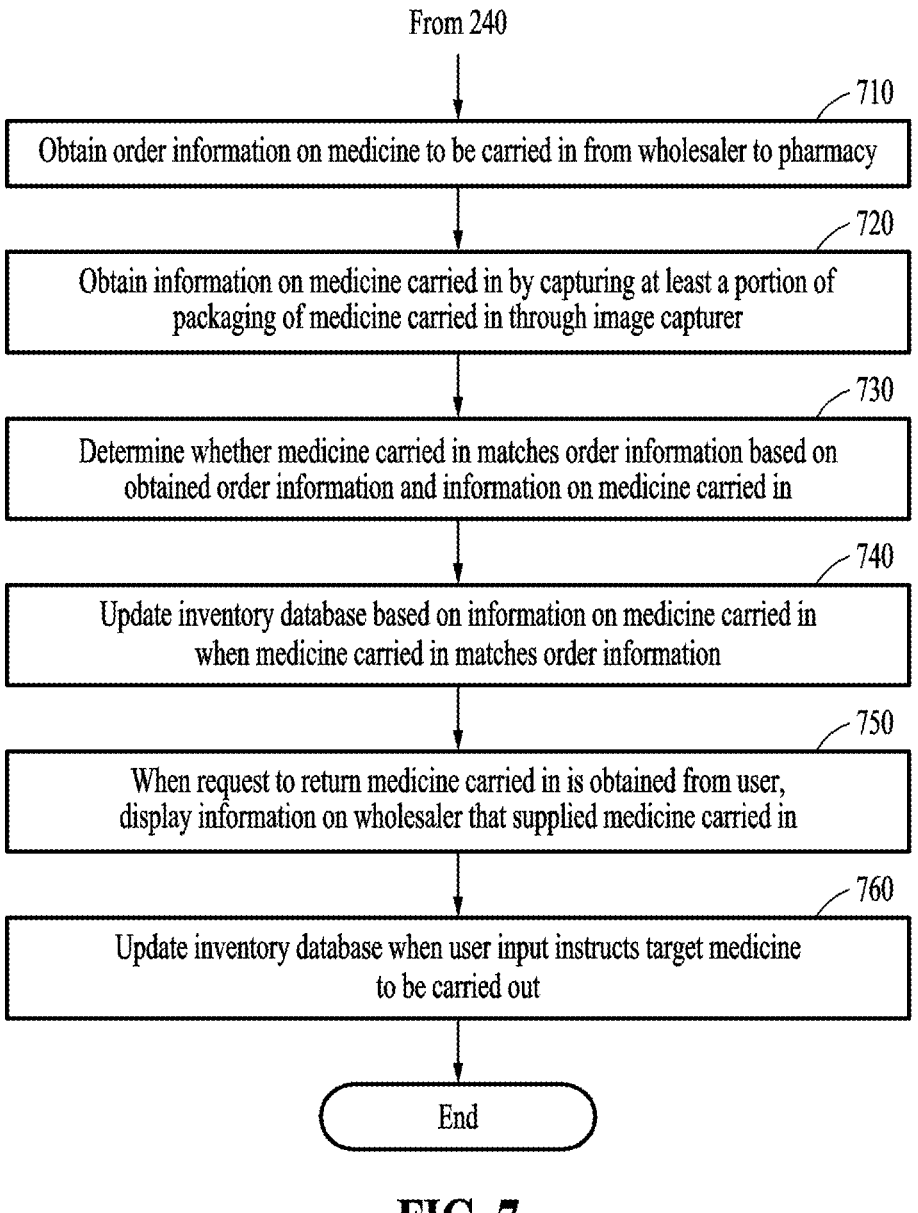

From 240

710

Obtain order information on medicine to be carried in from wholesaler to pharmacy

720

Obtain information on medicine carried in by capturing at least a portion of packaging of medicine carried in through image capturer

730

Determine whether medicine carried in matches order information based on obtained order information and information on medicine carried in

740

Update inventory database based on information on medicine carried in when medicine carried in matches order information

750

When request to return medicine carried in is obtained from user, display information on wholesaler that supplied medicine carried in

760

Update inventory database when user input instructs target medicine to be carried out End

FIG. 7

MEDICINE PREPARATION ASSISTANCE DEVICE, METHOD FOR OPERATING SAME, AND APPLICATION

TECHNICAL FIELD

Hereinafter, a technique for determining whether a medicine matches prescription information is disclosed.

BACKGROUND ART

In the related art, pharmacies do not have an electronic, systematic system to inspect medicines dispensed by a pharmacist. The pharmacist has to personally check with his or her own eyes whether a medicine he or she gives out is the same as the medicine prescribed. No matter how carefully the pharmacist may check the medicine, due to human error, the pharmacist may make a mistake. For example, pharmacies typically have a large number of prescriptions that need to be processed urgently, leaving the pharmacist with very little time to determine whether the medicine being given out is the same as the medicine prescribed. In particular, in the case of large pharmacies near university hospitals, the number of prescriptions to be processed per hour is higher than usual, so pharmacists may have even less time to inspect the medicine. In addition, the pharmacist may have difficulty reading the small print on medicine boxes due to aging.

In pharmacies as well as large hospital pharmacies, since pharmacists and/or nurses handle a variety of prescribed injections, they may confuse injections with similar appearances, label colors, and spellings (e.g., NaCl and KCl, Dobutamine and Dopamine, Tabactam and Uniperatam, Keratam and Keppra, H-lase and H-2 Injection, and the like).

In the case of injections especially, since they are injected directly into the bloodstream unlike orally administered medicine, it may have fatal effects.

Injections are delivered directly into the bloodstream through the blood vessels, so they may work faster than orally administered medicine. In addition, injections may take effect quickly even in small doses. Therefore, when the wrong medicine is injected, it may spread quickly into the body at high concentrations, which may be fatal.

When an incorrectly prepared medicine or injection is delivered to a patient, it may pose a health risk to the individual patient and may result in loss of time and money for the pharmacy and/or hospital. Thus, a technique to inspect the medicine dispensed by pharmacists and/or nurses may be required.

SUMMARY OF THE INVENTION

A preparation assistance method performed by an electronic device may include obtaining prescription information corresponding to the prescription based on an image obtained by capturing at least a portion of the prescription through the image capturer, determining a total quantity of a prescribed medicine based on the obtained prescription information, determining the package counts of a plurality of available packaging of the prescribed medicine based on the determined total quantity of the prescribed medicine, and displaying the determined package counts through an output unit.

The obtaining of the prescription information may include obtaining in-hospital prescription information within a hospital and skipping the obtaining of the prescription information through the image capturer in response to obtaining the in-hospital prescription information.

The determining of the total quantity of the prescribed medicine may include calculating the total quantity of the prescribed medicine based on a single dose, the number of doses per day, and the total number of days of medication of the prescribed medicine.

The determining of the total quantity of the prescribed medicine may include determining a daily dosage of the prescribed medicine by adding up single doses for each time of administration, in response to the number of doses per day of the prescribed medicine being two or more and the single doses of the prescribed medicine being different depending on the time of administration, and calculating the total quantity of the prescribed medicine by multiplying the total number of days of medication of the prescribed medicine by the determined daily dosage.

The determining of the total quantity of the prescribed medicine may include, when the prescribed medicine has a different single dose depending on a medication period, determining a dosage for the medication period by multiplying the number of days of medication for each medication period and a single dose of the corresponding medication period, and calculating the total quantity of the prescribed medicine by adding up the dosages for a plurality of medication periods.

The determining of the total quantity of the prescribed medicine may include, when the prescribed medicine is a syrup type or ointment type, calculating the total quantity of the prescribed medicine based on a unit dosage of the prescribed medicine, along with the single dose, the number of doses per day, and the total number of days of medication of the prescribed medicine.

The preparation assistance method may further include further displaying the content of an active ingredient of the prescribed medicine together with the name of the prescribed medicine through the output unit, when the content of the active ingredient of the prescribed medicine is not stated in the prescription.

The preparation assistance method may further include determining whether to package a first prescribed medicine and a second prescribed medicine together based on at least one of the number of days of medication or regimen of each of the first prescribed medicine and the second prescribed medicine, based on the prescription information, and when it is determined that the first prescribed medicine and the second prescribed medicine are not to be packaged together, displaying a guidance message for separate packaging of the first prescribed medicine and the second prescribed medicine through the output unit.

The determining of the package counts of the plurality of packaging may include determining a first quantity combination including the package counts of the plurality of packaging for the total quantity of the prescribed medicine, and determining a second quantity combination in which the package count of at least one packaging is different from the first quantity combination, for the total quantity of the prescribed medicine.

The preparation assistance method may further include, when the prescribed medicine is a medicine prohibited from being opened, displaying a guidance message through the output unit informing that the prescribed medicine may not be opened.

Each of the plurality of available packaging of the prescribed medicine may include a different quantity of the prescribed medicine in dosage form.

The determining of the package counts of the plurality of packaging may include determining the package counts of a plurality of available packaging for each of the prescribed medicine, when the prescription information includes a plurality of prescribed medicines.

The preparation assistance method may further include obtaining packaging type information corresponding to a packaging by capturing at least a portion of the packaging of a target medicine through the image capturer, determining whether the target medicine may be given out by verifying whether the target medicine is the same medicine as the prescribed medicine, based on the packaging type information, and displaying whether the target medicine may be given out through the output unit.

The determining of whether the target medicine may be given out may include, based on the packaging type information and the prescription information, determining whether a name, content of an active ingredient, dosage form, and packaging type of the prescribed medicine match a name, content of an active ingredient, dosage form, and packaging type of the target medicine.

The determining of whether the target medicine may be given out may include determining a limit on an expiration date of the prescribed medicine, based on prescription date information, the total number of days of medication, and a grace period of the prescribed medicine among the prescription information, determining that the target medicine may be given out, when an expiration date of the target medicine included in the packaging type information is later than the limit on the expiration date of the prescribed medicine, and determining that the target medicine may not be given out, when the expiration date of the target medicine included in the packaging type information is earlier than the limit on the expiration date of the prescribed medicine.

The preparation assistance method may further include obtaining an image of the target medicine packaged in a pill pouch bag through the image capturer when the target medicine is packaged in a pill pouch bag.

The preparation assistance method may further include obtaining an image of a scene where the target medicine is delivered to a patient through the image capturer, when a user input instructing the target medicine to be given out is obtained.

The preparation assistance method may further include obtaining order information on a medicine to be brought in to a pharmacy from a wholesaler, obtaining information on the medicine brought in by capturing at least a portion of a packaging of the medicine brought in through the image capturer, determining whether the medicine brought in matches the order information based on the obtained order information and the information on the medicine brought in, and updating an inventory database based on the information on the medicine brought in, when the medicine brought in matches the order information.

The preparation assistance method may further include displaying information on the wholesaler that supplied the medicine brought in when a request to return the medicine brought in is obtained from a user.

The preparation assistance method may further include receiving a user input instructing whether to give out a target medicine from a user, and updating the inventory database, when the user input instructs the target medicine to be given out.

An electronic device according to an embodiment may include an image capturer configured to capture at least a portion of a prescription, a processor configured to obtain prescription information corresponding to the prescription based on an image obtained by capturing at least a portion of the prescription through the image capturer, determine a total quantity of a prescribed medicine based on the obtained prescription information, and determine the package counts of a plurality of available packaging of the prescribed medicine based on the determined total quantity of the prescribed medicine, and an output unit configured to display the determined package counts.

These and other features and advantages of the invention will become apparent to those skilled in the art from the following detailed description and the accompanying drawings. It should be understood, however, that the detailed description and specific examples, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF DRAWINGS

Preferred exemplary embodiments of the invention are illustrated in the accompanying drawings in which like reference numerals represent like parts throughout, and in which:

FIG. 3 is a flowchart illustrating an operation of displaying a guidance message by an electronic device according to various embodiments.

FIG. 5 is a flowchart illustrating an example of a preparation assistance method including an operation of determining and displaying whether a target medicine may be given out according to various embodiments.

FIG. 7 is a flowchart illustrating an example of a preparation assistance method including an operation of managing an inventory database based on medicines brought in from a wholesaler and medicines given out to patients according to various embodiments.

DETAILED DESCRIPTION OF THE INVENTION

Figure 1:
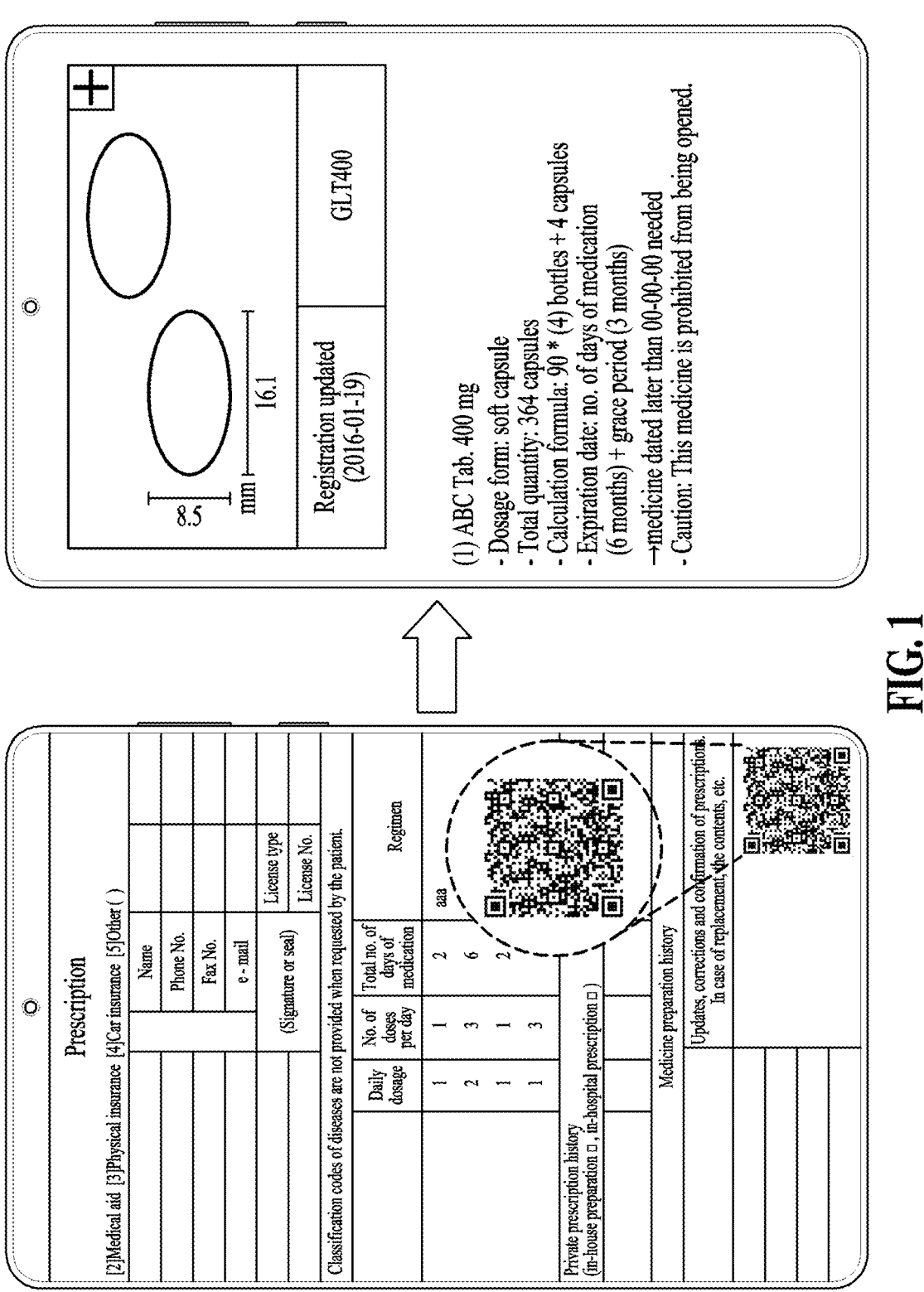
FIG. 1 illustrates an example of an interface for medicine identification in an electronic device according to various embodiments.

The following detailed structural or functional description is provided as an example only and various alterations and modifications may be made to embodiments. Accordingly, the embodiments are not construed as limited to the disclosure and should be understood to include all changes, equivalents, and replacements within the idea and the technical scope of the disclosure.

Although terms, such as first, second, and the like are used to describe various components, the components are not limited to the terms. These terms should be used only to distinguish one component from another component. For example, a first component may be referred to as a second component, and similarly, the second component may also be referred to as the first component.

It should be noted that if it is described that one component is "connected", "coupled", or "joined" to another component, a third component may be "connected", "coupled", and "joined" between the first and second components, although the first component may be directly connected, coupled, or joined to the second component.

The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Hereinafter, embodiments will be described in detail with reference to the accompanying drawings. When describing the embodiments with reference to the accompanying drawings, like reference numerals refer to like elements and a repeated description related thereto will be omitted.

FIG. 1 illustrates an example of an interface for medicine identification in an electronic device according to various embodiments.

FIG. 1 is merely an example of a user interface design and may be modified according to the design.

When a prescription is received at a pharmacy, a user (e.g., a pharmacist) may capture the prescription with an electronic device. The electronic device may include an image capturer (e.g., a camera) and may obtain an image corresponding to the prescription through the image capturer.

According to an embodiment, the electronic device may capture a quick response (QR) code included in the prescription based on a user input. The electronic device may obtain an image of a portion corresponding to the QR code in the prescription.

The QR code may include prescription information related to at least one of a name, manufacturer, quantity, regimen, or content of an active ingredient of a prescribed medicine, for example. The prescription information is not limited to the at least one of the name, manufacturer, quantity, regimen, or content of an active ingredient of the prescribed medicine, and the prescription information may also include other information related to the prescribed medicine. As another example, the QR code may include access information (e.g., a link to access information related to a medicine) related to a medicine. The electronic device may obtain the prescription information by reading the image corresponding to the QR code. In addition, the electronic device may input the obtained prescription information to a pharmacy program. Also, when the pharmacy program is linked to an automatic preparation machine installed in the pharmacy, the automatic preparation machine may package the medicine into single pill pouch bags based on the input prescription information. The pharmacist may give out a medicine to be additionally provided to a patient, separate from the pill pouch bag(s) packaged by the automatic preparation machine.

According to an embodiment, the electronic device may obtain prescription information from an image (e.g., a prescription image) corresponding to a prescription using character detection (e.g., optical character recognition (OCR)). For example, the electronic device may recognize characters from a prescription image based on OCR and determine the prescription information from the recognized characters.

The pharmacist may prepare a medicine as indicated on the prescription, but mistakes by the pharmacist may occur due to the varying content of active ingredients, manufacturers, or quantities of each medicine. In large pharmacies and/or hospital pharmacies with a plurality of pharmacists, a plurality of human inspection processes may be performed to reduce these errors. Most errors may be identified through the inspection process before the medicine is delivered to the patient, but because the inspection process is time-consuming and done by people, mistakes may still occur, such as giving out the wrong medicine, despite the inspection process. Also, when there is only one pharmacist working, the errors may be fatal because there is no other pharmacist to inspect the medicine. To compensate for the errors, most pharmacists (or pharmacies) may be enrolled in pharmacy insurance. In the case of pharmacies, mistakes may not be allowed since the pharmacies handle medicines that affect life.

The electronic device (also referred to herein as, a "drug match (DM) device") according to an embodiment may display at least one of the content of an active ingredient of a medicine, a dosage form classification of the medicine, the total quantity of the medicine, a calculation formula to be prepared for each medicine (e.g., the package count of an available packaging), or a limit on an expiration date, when a QR code of a prescription is captured. However, the electronic device is not limited to displaying at least one of the content of the active ingredient of the medicine, the dosage form classification of the medicine, the total quantity of the medicine, the calculation formula to be prepared for each medicine, or the limit on the expiration date, and the electronic device may also display prescription information and/or information derived from the prescription information. For example, as shown in FIG. 1, the electronic device may display various information when the QR code of the prescription is captured. Examples of each piece of information are described below.

(1) Name of prescribed medicine (e.g., AAA) and content (e.g., 10 mg, 20 mg, 40 mg, or 80 mg) of active ingredient (2) Dosage form classification of prescribed medicine For example, in the case of BBB, the dosage form classification may be one of an eye ointment, otic solution, and eye drops, or in the case of CCC, one of a tablet, sustained-release tablet, OD tablet, sublingual tablet, capsule, and sustained-release capsule, or in the case of DDD, one of an ointment, cream, lotion, and gel, or in the case of EEE, one of a patch, vaginal suppository, and syrup.

(3) Total quantity (e.g., 60 tablets in total when taken 3 times a day for 20 days, 10 tablets in total when taken 1 time every other day for 20 days) of prescribed medicine The electronic device may calculate the total quantity of each medicine when the total number of days of medication for each prescribed medicine is different. The electronic device may calculate the total quantity of a medicine when a single dose and/or frequency of administration is different.

(4) Package count of available packaging for prescribed medicine

An available packaging for a prescribed medicine may have a packaging type and packaging unit in which the medicine is manufactured and/or supplied commercially. The packaging type may be at least one of a box, bottle, or plate type, for example. As will be described later, a packaging corresponding to each packaging type (e.g., box, bottle, or plate type) may contain a medicine in a dosage form (e.g., a capsule, tablet, or tube). The dosage form and/or packaging unit (e.g., the number of medicines in the dosage forms contained in a packaging of a packaging type) may vary by packaging type. In addition, even when the packaging types are the same, there may be packaging with different packaging units. The electronic device may automatically provide a calculation formula (e.g., the package count by packaging type) for all medicines that are given out, thereby reducing calculation errors and errors in giving out medicines caused by different packaging types and different packaging units for the same medicine.

(5) Limit on expiration date

A limit (or a minimum limit date) on an expiration date may be an expiration date required for a medicine to be provided to a patient based on a date that the medicine is prepared, which may be, for example, a date on which medication according to the prescription is expected to be completed from the date of prescription. The electronic device may calculate a limit on an expiration date based on the number of days of medication and/or medication period of the prescribed medicine and display the limit on the expiration date.

According to an embodiment, the electronic device may calculate a limit on an expiration date considering the number of days of medication from a current date, and display the calculated limit on the expiration date. For example, the electronic device may display a message indicating that a medicine with an expiration date of 4 months or more from the current date (e.g., the prescription date) is to be retrieved when the number of days of medication of the prescribed medicine is 120 days (e.g., 4 months). For example, the electronic device may display a message indicating to retrieve a medicine with an expiration date after July 10th, which is at least 120 days (e.g., 4 months) from the current date, when the current date is March 10th and the number of days of medication is 120 days (e.g., 4 months).

According to an embodiment, the electronic device may calculate a limit on an expiration date considering the medication period from a current date, and display the calculated limit on the expiration date. The medication period may include a grace period (or margin period) along with the number of days of medication. The grace period may be a period during which a patient (e.g., a patient with low medication compliance) may be likely to stop taking a medication, and may be determined to prepare for cases in which the completion of medication is delayed longer than the number of days of medication. For example, the electronic device may display a guidance message indicating to retrieve a medicine with an expiration date after December 10th, when the current date is March 10th, the number of days of medication is 90 days (e.g., 3 months), and the grace period is 6 months. In this example, the grace period may be specified as 3 months, 4 months, and/or 6 months, depending on the preference of a pharmacist using the DM device.

The electronic device may capture a QR code on a medicine bottle to obtain an expiration date of a medicine and compare the expiration date to a limit on the expiration date. For example, the electronic device may display the expiration date of the medicine and the calculated minimum limit date side by side on the same screen of the electronic device in the same date display format (e.g., year/month/day format). In another example, the electronic device may calculate a remaining period of the medicine from the calculated minimum limit date to the expiration date of the medicine to be given out, and display the calculated remaining period. The remaining period may be determined based on the minimum limit date deducted from the expiration date of the medicine to be given out. When the expiration date is earlier than the minimum limit date, the electronic device may calculate a shortage period and display the calculated shortage period. The shortage period may be determined based on the minimum limit date minus the expiration date of the medicine to be given out. For example, in the case of medicines imported from abroad, when an expiration date of a medicine is not expressed in a year/month/day format, but in a different format (e.g., month/day/year or day/month/year), mistakes by pharmacists may occur. However, by capturing a QR code of each container and checking the expiration date of a medicine to be given out through the electronic device, the medicine with an expiration date that is after a limit (e.g., a minimum limit date) on the expiration date may be accurately given out. For example, in the case of a medicine that is to be administered for 3 months and is to be given out on March 10th, an additional 6-month grace period may be granted so that a medicine with an expiration date after December 10th may be given out. The potential for errors to occur when performed by a pharmacist may be significantly reduced.

(6) Whether a prescribed medicine matches the medicine to be given out

When a QR code on a medicine bottle is captured, the electronic device may determine and display whether the QR code on the medicine bottle matches a medicine that is based on prescription information. For example, when a pharmacist retrieves a medicine and captures the QR code on the medicine bottle with the electronic device, the electronic device may determine and display whether the QR code on the medicine bottle that is captured matches (e.g., indicated by "O") the prescription information or does not match (e.g., indicated by "X") the prescription information. The electronic device may capture the pills brought by the pharmacist and, through information linked to the Korea Pharmaceutical Information Center and an OCR function, determine and/or display whether the pills retrieved by the pharmacist match the medicine (i.e., the prescribed medicine) that is based on the prescription information.

As will be described in more detail later, the electronic device according to an embodiment may capture a medicine to be given out and store the captured image in a storage space of the electronic device, and the captured image may be used as evidence of whether the medicine has been accurately prepared and given out.

In addition, when a medicine is brought in from a wholesaler to a pharmacy, the electronic device may easily determine an inventory of medicines by linking with the pharmacy program and inputting information (e.g., the name of the medicine, the content of an active ingredient, a packaging type, and the package count per packaging) on the medicine being brought in as shown in a transaction statement. Furthermore, the electronic device may determine how much medicine is required from the pharmacy each month based on the accumulated information and display the required inventory quantity. Management of the inventory database is described in more detail below with reference to FIG. 7.

Hereinafter, a preparation assistance method performed by the electronic device according to an embodiment is described.

Figure 2:
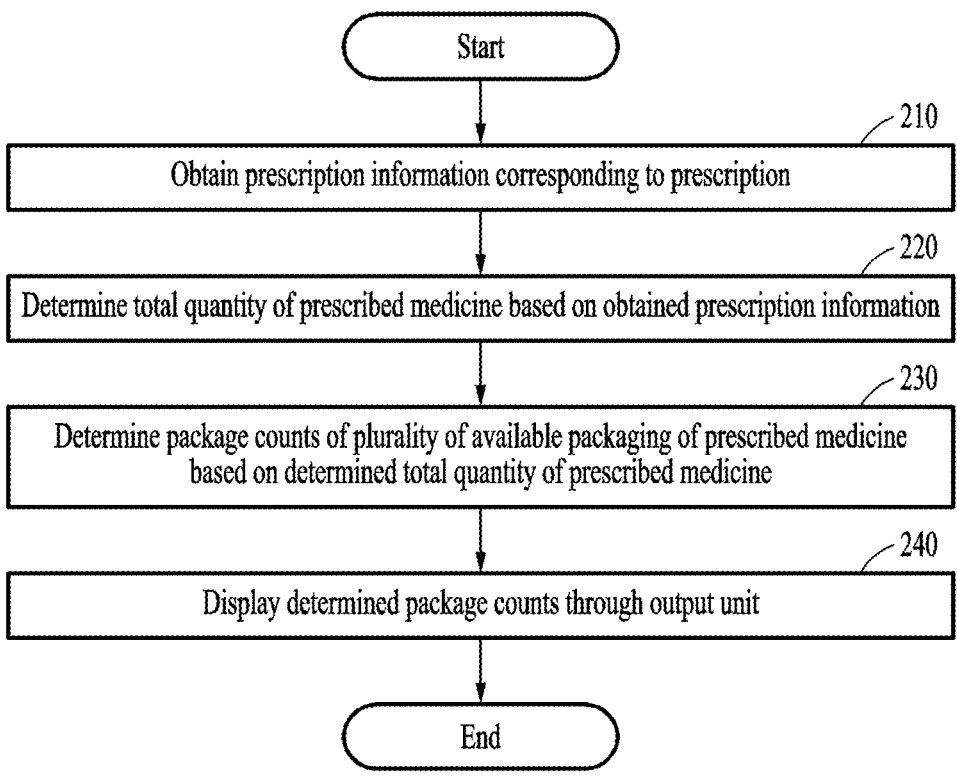
FIG. 2 is a flowchart illustrating an example of a preparation assistance method according to various embodiments.

FIG. 2 is a flowchart illustrating an example of a preparation assistance method according to various embodiments.

In operation 210, the electronic device may obtain prescription information corresponding to a prescription.

According to an embodiment, the electronic device may obtain the prescription information based on an image obtained by capturing at least a portion of the prescription through an image capturer. For example, the electronic device may obtain the prescription information by applying OCR to the prescription. In another example, the electronic device may obtain the prescription information based on an image of a QR code included in the prescription. The prescription information may include information on a prescribed medicine. The information on the prescribed medicine may include at least one of, for example, a name, manufacturer, regimen, single dose, number of doses per day, number of days of medication, or content of an active ingredient of a medicine.

In an embodiment, the electronic device may obtain the prescription information from another electronic device (e.g., a hospital server). The electronic device may obtain in-hospital prescription information within a hospital. The electronic device may skip the operation of obtaining the prescription information through the image capturer in response to obtaining the in-hospital prescription information. For example, when a prescription (e.g., an in-hospital prescription) is filled within a hospital, the electronic device may receive prescription information from the hospital server.

In operation 220, the electronic device may determine the total quantity of a prescribed medicine based on the obtained prescription information.

In an embodiment, the electronic device may calculate the total quantity of prescribed medicine based on the prescription information. For example, the electronic device may calculate the total quantity of prescribed medicine based on a single dose, the number of doses per day, and the total number of days of medication of the prescribed medicine. The electronic device may display the total quantity of prescribed medicine through an output unit.

For example, the electronic device may calculate the total quantity of medicine when the number of doses per day is two or more and a single dose differs depending on the time of administration. The electronic device may determine a daily dosage of the prescribed medicine by adding up the single doses for each time of administration, when the number of doses per day is two or more and the single dose differs depending on the time of administration. The electronic device may calculate the total quantity of the prescribed medicine by multiplying the total number of days of medication of the prescribed medicine by the determined daily dosage. An example of the aforementioned case is described in more detail in Example 5 below.

In another example, the electronic device may calculate the total quantity of the prescribed medicine based on a tapering regimen. The tapering regimen may refer to a patient being prescribed different single doses of a particular medicine depending on the medication period. When the prescribed medicine has different single doses depending on the medication period, the electronic device may determine a dosage for a corresponding medication period by multiplying the number of days of medication for each medication period by the dosage for the corresponding medication period. The electronic device may calculate the total quantity of the prescribed medicine by adding up dosages for a plurality of medication periods. An example of the aforementioned case is described in more detail in Example 9 below.

In another example, the electronic device may calculate the total quantity of the prescribed medicine when the prescribed medicine is a syrup type or ointment type. For example, when the prescribed medicine is a syrup type or ointment type, the electronic device may calculate the total quantity of the prescribed medicine based on a unit dosage of the prescribed medicine, along with the single dose, the number of doses per day, and the total number of days of medication of the prescribed medicine. For example, the electronic device may calculate the total quantity of a syrup-type or ointment-type medicine by multiplying the single dose, the number of doses per day, the total number of days of medication, and the unit dosage. An example of the aforementioned case is described in more detail in Example 10 below.

In addition, in the case of general ointments, eye drops, and inhalants, the electronic device may capture a QR code to match the number of medications being given out.

In operation 230, the electronic device may determine the package count of an available packaging of the prescribed medicine based on the determined total quantity of the prescribed medicine.

The electronic device may determine the package count in the available packaging based on the total quantity of the prescribed medicine. The electronic device may identify the available packaging for the prescribed medicine. The available packaging may be a packaging that may be given out for the corresponding medicine. The available packaging may contain as many dosage forms of the medicine as the packaging unit in the corresponding packaging type as described above. The electronic device may determine a packaging in which the prescribed medicine is manufactured, sold, and supplied and/or a packaging (e.g., a packaging prepared in stock) available at a pharmacy. For example, the electronic device may identify an available packaging type and available packaging unit of a medicine that matches prescription information from an inventory database of the pharmacy. The available packaging type and available packaging unit may be the packaging type and packaging unit of a packaging in the inventory of the pharmacy for the corresponding medicine. The electronic device may determine the package count per packaging for the total quantity of the prescribed medicine when there is a plurality of packaging available for the prescribed medicine. The packaging unit may be defined as the number of medicines in a dosage form contained in each packaging. The dosage form (or unit dosage form) may be a form in which the corresponding medicine is administered to a patient as a unit dosage, and may include, for example, a capsule, a tablet, a tube, or an ampoule. For reference, the prescribed medicine may be an injection, and when the prescribed medicine is an injection, the dosage form of the prescribed medicine may be an ampoule.

For example, the dosage form of a particular medicine may be a tablet form. The packaging type of a particular medicine may be one of a first packaging type (e.g., a box type), a second packaging type (e.g., a bottle type), or a third packaging type (e.g., a plate type). A packaging of the first packaging type (e.g., the box type) may contain a first packaging unit (e.g., 24) of tablet-form medicine, a packaging of the second packaging type (e.g., the bottle type) may contain a second packaging unit (e.g., 18) of tablet-form medicine, and a packaging of the third packaging type (e.g., the plate type) may contain a third packaging unit (e.g., 5) of tablet-form medicine. However, the packaging unit may be different even when the packaging type is the same.

As an example, the total quantity of a prescribed medicine may be 80 tablets, the first packaging type of the prescribed medicine may contain 28 tablets, the second packaging type of the prescribed medicine may contain 100 tablets, and the third packaging type (e.g., the plate-type packaging) of the prescribed medicine may contain 7 tablets. The electronic device may determine the package count of the first packaging type to be 2, the package count of the second packaging type to be 0, and the package count of the third packaging type to be 3 and determine 3 single tablets, to prepare 80 tablets (28*2+7*3+3=80).

In an embodiment, the prescription information may include information on a plurality of prescribed medicines. The electronic device may determine the package counts of the packaging of each of the plurality of prescribed medicines based on the obtained prescription information. The electronic device may determine, for each prescribed medicine, the package counts of the plurality of packaging available for the corresponding prescribed medicine. The packaging available for the plurality of prescribed medicines and/or the total quantity of the plurality of prescribed medicines may vary. The electronic device may determine the package counts of the available packaging for each prescribed medicine, based on the prescribed medicine.

In an embodiment, the electronic device may determine the package count of each packaging type by considering the inventory quantity of packages of each packaging type based on an inventory database. As will be described in more detail with reference to FIG. 7, the inventory database may include inventory information by packaging type of medicines that are held and/or may be given out from a pharmacy. For example, the inventory database may store the package count in stock of the first packaging type of a prescribed medicine to be 3. The electronic device may determine, for each packaging type of the prescribed medicine, the package count of the corresponding packaging type to be a value less than or equal to an inventory quantity of the corresponding packaging type stored in the inventory database.

In an embodiment, the electronic device may determine the package count of a corresponding packaging type by considering a recommended stock quantity of each packaging type of the prescribed medicine. The recommended stock quantity for a packaging type of a medicine may be a stock quantity set as a standard for a packaging type of a medicine. The recommended stock quantity may be determined (e.g., set, changed, adjusted) by a user (e.g., a pharmacist). The electronic device may adjust the giving out and bringing in of medicines so that the stock quantity is greater than or equal to the recommended stock quantity of the packaging type of a medicine. For example, the electronic device may determine the package count of a packaging type to be less than or equal to the package count of the packaging type in stock minus the recommended stock quantity of the packaging type, so that the pharmacy may maintain more than the recommended stock quantity of each packaging type of the prescribed medicine. For example, when the stock quantity of a prescribed medicine of a bottle type is 10 (e.g., 10 bottles) and the recommended stock quantity of the prescribed medicine of the bottle type is 5, the electronic device may determine the package count of the prescribed medicine of the bottle type to be 5 or less. An example of adjusting the bringing in of medicine based on the recommended inventory quantity is described in more detail below with reference to FIG. 7.

In operation 240, the electronic device may display the determined package counts through an output unit. The electronic device may provide a guide to the user on giving out medicine by displaying the package count of each of the plurality of packaging available for a prescribed medicine.

According to an embodiment, when the content of an active ingredient of a prescribed medicine is not stated in the prescription, the electronic device may further display the content of the active ingredient of the prescribed medicine together with the name of the prescribed medicine through the output unit. For example, when the content of the active ingredient of the prescribed medicine is not stated in the prescription and there is another medicine with the same name as the prescribed medicine but a different content of the active ingredient, the electronic device may further display the content of the active ingredient of the prescribed medicine together with the name of the prescribed medicine.

As an example, the name of a first medicine and a second medicine may be AAA, the content of an active ingredient of the first medicine may be 500 mg, and the content of an active ingredient of the second medicine may be 1000 mg. The first medicine may be written as "AAA" on the prescription, and the second medicine may be written as "AAA 1000 mg" on the prescription. In other words, the first medicine may only have the name of the medicine stated on the prescription, and the content of the active ingredient of the first medicine may not be stated. In this case, in order to prevent and/or reduce the user (e.g., the pharmacist) from confusing "AAA" indicating the first medicine in the prescription with the second medicine (e.g., listed as "AAA 1000 mg"), the electronic device may further display (e.g., display "AAA 500 mg") the content of the active ingredient of the medicine together with the name of the medicine to indicate the first medicine through the output unit, when the content (e.g., 500 mg) of the active ingredient of the first medicine is not written in the prescription.

In an embodiment, the electronic device may determine and/or display a plurality of combinations of quantities for the total quantity of prescribed medicine. The quantity combination may be a combination (e.g., a packaging quantity combination) of the package counts of an available packaging of a prescribed medicine. For example, the electronic device may determine a first quantity combination including the package counts of a plurality of packaging, for the total quantity of the prescribed medicine. The electronic device may determine a second quantity combination in which the package count of at least one packaging is different from the first quantity combination, for the total quantity of the prescribed medicine.

When the electronic device obtains a user input for selecting one of a plurality of quantity combinations, the electronic device may provide a guide including the selected quantity combination. According to an embodiment, the electronic device may further display a recommendation graphical representation corresponding to at least one of the plurality of quantity combinations to the user based on a predetermined priority. The priority for the quantity combination may be determined based on at least one of, for example, the sum of the quantities, the package count of a packaging in which the quantity is determined to be one or more, or the characteristics of the prescribed medicine. The electronic device may determine whether a target medicine brought by the user may be given out based on the selected quantity combination. The determining of whether the target medicine may be given out is described in more detail below with reference to FIG. 5.

For example, a prescribed medicine may be given out in a box-type packaging of 40 tablets, a bottle-type packaging of 20 tablets, and/or a tablet-type packaging of 10 tablets. The electronic device may determine a plurality of quantity combinations when the total quantity of prescribed medicine is determined to be 100 tablets. For simplicity of notation, hereinafter the examples of quantity combinations may be expressed as one-dimensional vectors having elements corresponding to the number of the box types, the number of the bottle types, and the number of the plate types, in that order. The electronic device may determine a first quantity combination (e.g., [2, 1, 0]), a second quantity combination (e.g., [2, 0, 2]), a third quantity combination (e.g., [1, 3, 0]), and a fourth quantity combination (e.g., [0, 0, 10]) for the total quantity of prescribed medicine. The electronic device may obtain a user input selecting the first quantity combination from among a plurality of quantity combinations. The electronic device may provide a guide to the user regarding giving out a prescribed medicine in the first quantity combination, that is, giving out 2 boxes and 1 bottle of the prescribed medicine.

For example, a prescribed medicine may be given out in a bottle-type packaging of 100 tablets, a box-type packaging of 56 tablets, and/or a plate-type packaging of 14 tablets. The electronic device may determine a plurality of quantity combinations when the total quantity of prescribed medicine is determined to be 180 tablets. The first quantity combination may include 3 units of the box-type packaging and 12 units of the tablet-type in dosage form. In other words, the first quantity combination may correspond to 3 boxes and 12 tablets of the prescribed medicine. The second quantity combination may include 1 unit of the bottle-type packaging and 80 units of the tablet type. In other words, the second quantity combination may correspond to 1 bottle and 80 tablets of the prescribed medicine.

Hereinafter, various examples of determining the package counts of an available packaging of a prescribed medicine are described.

Example 1: (when Prescribed in Bottle Units) the Package Count Per Packaging of a Medicine May be Automatically Calculated (where the Unit of Bottles and the Unit of Individual Medicine are Distinguished)

1-1. When AAA 220 Tablets are Prescribed,

A package of the first packaging type (e.g., bottle) of medicine AAA may contain 84 tablets, and a package of the second packaging type (e.g., plate) may contain 21 tablets. For the giving out of AAA 220 tablets, the electronic device may determine to give out 2 packages of the first packaging type, 2 packages of the second packaging type, and 10 unit tablets. For example, for the giving out of AAA 220 tablets, 2 bottles (e.g., 84×2 tablets) of AAA, 2 plates (e.g., 21×2 tablets) of AAA, and 10 AAA tablets may be delivered to a patient.

$$84\times2+21\times2+10=220 \qquad \text{Example formula:}$$

1-2. When BBB 50/500 mg 220 Tablets are Prescribed,

A package of the first packaging type (e.g., bottle) of BBB 50/500 mg may contain 56 tablets, and a package of the second packaging type (e.g., plate) may contain 14 tablets. For the giving out of BBB 50/500 mg 220 tablets, the electronic device may determine to give out 3 packages of the first packaging type, 3 packages of the second packaging type, and 10 unit tablets. For example, for the giving out of BBB 50/500 mg 220 tablets, 3 bottles (e.g., 56×3 tablets) of BBB 50/500 mg, 3 plates (e.g., 14×3 tablets) of BBB 50/500 mg, and 10 BBB 50/500 mg tablets may be delivered to the patient.

$$56\times3+14\times3+10=220 \qquad \text{Example formula:}$$

1-3. When CCC 10 mg 65 Tablets are Prescribed,

A package of the first packaging type (e.g., bottle) of CCC 10 mg may contain 28 tablets, and a package of the second packaging type (e.g., plate) may contain 7 tablets. The electronic device may determine the quantity to be given out for the first packaging type, the second packaging type, and unit tablets. For example, for the giving out of CCC 10 mg 65 tablets, 2 bottles (e.g., 28×2 tablets) of CCC 10 mg, 1 plate (e.g., 7×1) of CCC 10 mg, and 2 CCC 10 mg tablets may be delivered to the patient.

$$28\times2+7\times1+2=65 \qquad \text{Example formula:}$$

1-4. When DDD 220 Capsules are Prescribed,

A package of the first packaging type (e.g., bottle) of DDD may contain 90 capsules, and a package of the second packaging type (e.g., plate) may contain 15 capsules. For the giving out of DDD 220 capsules, the electronic device may determine to give out 2 packages of the first packaging type, 2 packages of the second packaging type, and 10 unit tablets. For example, for the giving out of DDD 220 capsules, 2 bottles (e.g., 90×2 capsules) of DDD, 2 plates (e.g., 15×2) of DDD, and 10 DDD capsules may be delivered to the patient.

$$90\times2+15\times2+10=220 \qquad \text{Example formula:}$$

1-5. When AAA 10 mg 60 Tablets and BBB 1 mg 60 Tablets are Prescribed,

A package of the first packaging type (e.g., bottle) of AAA 10 mg may contain 90 tablets, and a package of the second packaging type (e.g., box) may contain 28 tablets. For the giving out of AAA 10 mg 60 tablets, the electronic device may determine to give out 2 packages of the second packaging type and 4 unit tablets. For example, for the giving out of AAA 10 mg 60 tablets, 0 packages (e.g., 90×0) of the first packaging type of AAA 10 mg, 2 packages (e.g., 28×2) of the second packaging type of AAA 10 mg, and 4 AAA 10 mg tablets may be delivered to the patient.

$$90\times0+28\times2+4=60 \qquad \text{Example formula:}$$

A package of the first packaging type (e.g., bottle) of BBB 1 mg may contain 100 tablets, and a package of the second packaging type (e.g., box) may contain 30 tablets. For the giving out of BBB 1 mg 60 tablets, the electronic device may determine to give out 2 packages of the second packaging type. For example, for the giving out of BBB 1 mg 60 tablets, 0 packages (e.g., 100×0) of the first packaging type of BBB 1 mg and 2 packages (e.g., 30×2) of the second packaging type of BBB 1 mg may be delivered to the patient.

$$100\times0+30\times2=60 \qquad \text{Example formula:}$$

1-6. When the content of an active ingredient is different among medicines with the same ingredients, mistakes may easily occur because packaging units of a plate are different. In other words, when the content of an active ingredient is different among medicines with the same ingredients, the number of dosage forms of medicines included in a package of the same packaging type (e.g., plate) may be different. For example, a packaging type (e.g., plate) of EEE 5 mg may contain a first packaging unit (e.g., 10) of tablets, and a packaging type (e.g., plate) of EEE 10 mg may contain a second packaging unit (e.g., 14) of tablets.

Since the number of tablets contained in each package of the first packaging type (e.g., bottle) and the number of tablets contained in each package of the second packaging type (e.g., plate) may be different for each medicine, and the number of days of medication and the number of times of administration are different for each prescription, it may be difficult to calculate a required number of tablets for each package of the medicine using a simple calculation formula. In particular, mistakes may easily occur when the number of tablets contained in the first packaging type and the second packaging type are different between similar medicines.

Hereinafter, various examples of calculating the total quantity of prescribed medicine are described.

Example 2: A Function for Calculating the Total Quantity

TABLE 1

| Name of prescribed medicine | Single dose | Number of doses per day | Total number of days of medication | Total quantity | Regimen |
|---|---|---|---|---|---|
| AAA 5 mg | 20 mg (4 tab) | 1 time/2 days | 60 days | 120 tab | Taken every other day at 7 am |
| BBB 25 mg | 3 cap (3 cap) | 1 time | 60 days | 180 cap | Take once a day |
| CCC | 1 cap (1 cap) | 1 time | 60 days | 60 cap | Take once a day before bed |
| DDD 10 mg | 1 tab (1 tab) | 1 time | 60 days | 60 tab | Take once a day before bed |
| EEE 15 g | | | | 2 tub | Apply twice a day |

Prescription information may not include the total quantity of medicine. The total quantity in Table 1 may not be included in the prescription information, but the electronic device may determine the total quantity based on the prescription information. For example, the prescription information may include the single dose, the number of doses per day, and the total number of days of medication, but may not explicitly include the total quantity of the prescribed medicine. The electronic device may calculate the total quantity of medicine based on the prescription information when the prescription information does not include the total quantity of medicine. For example, the electronic device may calculate the total quantity of medicine by multiplying the single dose, the number of doses per day, and the total number of days of medication. For example, in Table 1, the electronic device may calculate the total quantity of AAA 5 mg as 4 tablets×1 time/2 days×60 days=120 tablets.

Unlike Table 1, for example, in the case of AAA 5 mg taken every other day, the total number of days of medication in the prescription information may be 30 days, the number of doses per day in the prescription information may be 1 time, and the regimen in the prescription information may be to take every other day.

Example 3: A Function for Calculating the Total Quantity

TABLE 2

| Name of prescribed medicine | Single dose | Number of doses per day | Total number of days of medication | Total quantity | Regimen |
|---|---|---|---|---|---|
| AAA 5 ml | 1 pkg (1 pkg) | 1 time/7 days | 105 days | 15 pkg | Take once a week |

For example, in Table 2, the electronic device may calculate the total quantity of AAA 5 ml as 1 pkg×1 time/7 days×105 days=15 pkg. The pharmacist may bring 15 packages of AAA 5 ml and capture the packages with the electronic device. When the 15 packages of AAA 5 ml are captured, the electronic device may use artificial intelligence (AI) to determine whether there are 15 objects (e.g., packages) in the captured image. For example, the electronic device may use a machine learning-based model (e.g., a neural network model) to determine whether objects are present in a captured image. The machine learning-based models may be designed and trained to output whether objects are present in an image.

Example 4: Calculating the Total Quantity of a Medicine with an Unusually Different Number of Doses Per Day

TABLE 3

| Name of prescribed medicine | Single dose | Number of doses per day | Total number of days of medication | Total quantity | Regimen |
|---|---|---|---|---|---|
| AAA 80 mg | 1 tab | 1 time | 190 days | 190 tab | Take once a day after breakfast |
| BBB 150 mg/24000 IU | 1 tab | 1 time/30 days | 180 days | 6 tab | Take once a month |
| CCC | 1 tab | 1 time | 190 days | 190 tab | Take once a day after breakfast |

The electronic device according to an embodiment may calculate the total quantity of medicine taken over a long period of time (e.g., one month). For example, the electronic device may calculate the total quantity of a medicine taken once a month, such as BBB 150 mg/24000 IU shown in Table 4.

Example 5: Calculating the Total Quantity of Medicine when Each Dose is Different

TABLE 4

| Name of prescribed medicine | Single dose | Number of doses per day | Total number of days of medication | Total quantity | Regimen |
|---|---|---|---|---|---|
| AAA 10 mg | 15-5 mg (1.5-0.5 tab) | 2 times | 200 days | 400 tab | Take twice a day, 1 hour before breakfast and dinner |

TABLE 4-continued

| Name of prescribed medicine | Single dose | Number of doses per day | Total number of days of medication | Total quantity | Regimen |
|---|---|---|---|---|---|
| BBB 0.05 mg | 1 tab | 1 time | 200 days | 200 tab | Take once a day, 1 hour before breakfast |
| CCC 0.1 mg | 2 tab | 1 time | 200 days | 400 tab | Take once a day before bed |

The electronic device according to an embodiment may calculate the total quantity of a medicine based on the time of administration and a single dose, when the single dose of the medicine varies depending on the time of administration. For example, when a corresponding single dose in the morning is 1.5 tablets and a corresponding single dose in the evening is 0.5 tablets, such as AAA 10 mg in Table 5, the electronic device may calculate the total quantity of medicine for 200 days, which is the total number of days of medication, as 400 tablets, using, for example, an AI.

Example 6: Deriving a Preparation Formula for a Medicine (e.g., Artificial Tears) that Comes in Various Packaging Types (e.g., 30 Tubes, 60 Tubes, and the Like)

TABLE 5

| Name of prescribed medicine | Single dose | Number of doses per day | Total number of days of medication | Total quantity | Regimen |
|---|---|---|---|---|---|
| AAA disposable 0.45 mL/ tube | 1 | 1 time | 180 days | 180 | Apply eye drops frequently when eyes are dry |
| BBB disposable 0.45 mL/ tube | 1 | 1 time | 180 days | 180 | Apply eye drops frequently when eyes are dry |

The electronic device according to an embodiment may calculate the total quantity of AAA disposable 0.45 mL/tube as 1×1×180=180 tubes. The electronic device may determine and/or display the package count per packaging based on the total quantity of AAA disposable 0.45 mL/tube. For example, a package of a packaging type (e.g., box type) of AAA disposable 0.45 mL/tube may contain 60 tubes, and a package of a packaging type (e.g., box type) of BBB may contain 30 tubes. When a total quantity of 180 tubes each is prescribed for the AAA disposable 0.45 mL/tube and BBB 0.45 mL/tube, the electronic device may determine and/or display 3 boxes of AAA disposable 0.45 mL/tube and 6 boxes of BBB 0.45 mL/tube.

Example 7: Calculating the Total Quantity when the Number of Doses Per Day is Different

TABLE 6

| Name of prescribed medicine | Single dose | Number of doses per day | Total number of days of medication | Total quantity | Regimen |
|---|---|---|---|---|---|
| AAA 100 mg | 1 tab | 1 time | 28 days | 28 tab | Take once a day after breakfast |

TABLE 6-continued

| Name of prescribed medicine | Single dose | Number of doses per day | Total number of days of medication | Total quantity | Regimen |
|---|---|---|---|---|---|
| BBB 500 mg | 1 tab | 1 time/2 days | 28 days | 14 tab | Take every other day after breakfast |
| CCC | 1 tab | 1 time | 28 days | 28 tab | Take once a day after breakfast |
| DDD | 1 tab | 1 time | 28 days | 28 tab | Take once a day after breakfast |

The electronic device according to an embodiment may calculate the total quantity of medicine when the regimen of the medicine to take every other day. For example, in Table 6, since only BBB 500 mg is taken every other day, errors may easily occur when a pharmacist calculates the total quantity of the medicine. The electronic device according to an embodiment may reduce and/or prevent errors by a pharmacist by calculating the total quantity of medicine to be taken every other day and outputting the calculated result.

Example 8: Calculating the Total Quantity of a Specific Single Dose

TABLE 7

| Name of prescribed medicine | Single dose | Number of doses per day | Total number of days of medication | Total quantity | Regimen |
|---|---|---|---|---|---|
| AAA 300 mg | 300 mg (1 cap) | 1 time | 60 days | 60 cap | Take once a day, 30 minutes before breakfast |
| BBB 150 mg | 150 mg (1 cap) | 1 time | 60 days | 60 cap | Take once a day, 30 minutes before breakfast |
| CCC 250 mg | 250 mg (1 tab) | 1 time | 60 days | 60 tab | Take once a day before bed |
| DDD 400 mg | 700 mg (1.75 tab) | 1 time | 60 days | 105 tab | Take once a day before bed |
| EEE 15 mg | 1 tab | 1 time | 60 days | 60 tab | Take once a day before bed |

The electronic device according to an embodiment may calculate the total quantity of medicine when a single dose of the medicine is a real (e.g., a non-integer) number of tablets. For example, in Table 7, since a single dose of DDD 400 mg is 1.75 tablets, a mistake may be easily made by the pharmacist when calculating the total quantity of the medicine. The electronic device according to an embodiment may reduce and/or prevent mistakes by a pharmacist by automatically calculating the total quantity of a medicine to be administered in a single dose, which is a real number of tablets rather than an integer number of tablets.

Example 9: Calculating the Total Quantity of a
Tapering Regimen

TABLE 8

| Name of prescribed medicine | Single dose | Number of doses per day | Total number of days of medication | Total quantity | Regimen |
|---|---|---|---|---|---|
| AAA | 6 tab | 1 time | 14 days | 84 cap | Take once a day in the morning |
| AAA | 4 tab | 1 time | 14 days | 56 cap | Take once a day in the morning |
| AAA | 2 tab | 1 time | 14 days | 28 tab | Take once a day in the morning |
| AAA | 1 tab | 1 time | 14 days | 14 tab | Take once a day in the morning |
| BBB | 1 tab | 2 times | 56 days | 112 tab | Take twice a day, morning and evening |
| CCC | 6 tab | 1 time/7 days | 56 days | 48 tab | Take once every 7 days in the morning |

The electronic device according to an embodiment may calculate the total quantity of a medicine. For example, for the prescription information shown in Table 8, the electronic device may calculate the total quantity of AAA as 182 tablets, the total quantity of BBB as 112 tablets, and the total quantity of CCC as 48 tablets. The electronic device may reduce and/or prevent a pharmacist from making mistakes in calculating the total quantity of medicine by calculating and displaying the total quantity of medicine based on the prescription information, even when the total quantity of medicine is not included in the prescription information of a prescription.

The electronic device according to an embodiment may detect a medicine to be taken in a tapering regimen in the prescription information. A dosage may be reduced over time depending on the number of days the same type of medicine is administered. The electronic device may calculate the total quantity based on a single dose when the single dose is different for the same type of medicine, and may determine and/or display that the medicine is to be given out in separate packages based on the single dose.

For example, as shown in Table 8, AAA may be taken as 6 tablets once a day during the first 14 days, 4 tablets once a day during the second 14 days, 2 tablets once a day during the third 14 days, and 1 tablet once a day during the fourth 14 days. In this example, the electronic device may perform the calculation of the total quantity of AAA as 84 AAA tablets to be taken 6 tablets at a time for the first 14 days, 56 AAA tablets to be taken 4 tablets at a time for the second 14 days, 28 AAA tablets to be taken 2 tablets at a time for the third 14 days, and 14 AAA tablets to be taken 1 tablet at a time for the fourth 14 days. The electronic device may determine and/or display that the packaging is to be made separately for 84 AAA tablets for the first 14 days, 56 AAA tablets for the second 14 days, 28 AAA tablets for the third 14 days, and 14 AAA tablets for the fourth 14 days.

Example 10

TABLE 9

| Name of prescribed medicine | Single dose | Number of doses per day | Total number of days of medication | Total quantity | Regimen |
|---|---|---|---|---|---|
| AAA | 0.2 | 1 | 1 | 10 g | Apply once a day |

The electronic device according to an embodiment may calculate the total quantity of a medicine based on a unit dosage of the medicine. For example, in Table 9, when the unit dosage of AAA is 50 g, the electronic device may calculate the total quantity of AAA as 10 mg, by multiplying the unit dosage (e.g., 50 g) of AAA by a single dose (e.g., 0.2), the number of doses per day (e.g., 1), and the total number of days of medication (e.g., 1).

The electronic device may calculate the total quantity of a medicine based on a unit dosage of the medicine when the medicine included in prescription information is of a syrup type or ointment type. For example, the electronic device may determine whether the medicine included in the prescription information is of a syrup type or ointment type. When the medicine included in the prescription information is of the syrup type or ointment type, the electronic device may calculate the total quantity of the medicine by multiplying a single dose, the number of doses per day, the total number of days of medication, and a unit dosage of the medicine. As another example, when the medicine included in the prescription information is of a type (e.g., a tablet type) other than a syrup type or ointment type, the electronic device may calculate the total quantity of the medicine by multiplying the single dose, the number of doses per day, and the total number of days of medication, independently of the unit dosage of the medicine.

FIG. 3 is a flowchart illustrating an operation of displaying a guidance message by an electronic device according to various embodiments.

In an embodiment, the electronic device may determine a plurality of prescribed medicines based on prescription information. The prescription information may include, for each of the plurality of prescribed medicines, information on the prescribed medicine. The information on the prescribed medicine may include at least one of, for example, a name, content of an active ingredient, single dose, number of doses per day, total number of days of medication, or regimen of a medicine. Information on a first prescribed medicine may be independent (e.g., different) from information on a second prescribed medicine. The electronic device may determine whether to package the first prescribed medicine and the second prescribed in one pill pouch bag or give it out separately (e.g., in different pill pouch bags). As described above with reference to FIG. 2, the electronic device may determine and/or display the number (e.g., calculation formula) of packages for both the first prescribed medicine and the second prescribed medicine.

In operation 310, the electronic device may determine whether to package the first prescribed medicine and the second prescribed medicine together (e.g., package in one pill pouch bag), based on at least one of the number of days of medication or regimen of each of the first prescribed medicine and the second prescribed medicine, based on the prescription information. For example, the electronic device may determine not to package the first prescribed medicine and the second prescribed medicine together (e.g., package in different pill pouch bags) when the regimen (e.g., times of administration) of the first prescribed medicine and the second prescribed medicine are different. As another example, the electronic device may determine not to package the first prescribed medicine and the second prescribed medicine together when the number of days of medication of the first prescribed medicine and the second prescribed medicine are different. As another example, the electronic device may determine to package the first prescribed medicine and the second prescribed medicine together when the regimen and the number of days of medication of the first prescribed medicine and the second prescribed medicine are the same.

The electronic device may determine whether to package the first prescribed medicine together with a portion of the second prescribed medicine, when the regimen of the first prescribed medicine is the same as a portion of the regimen of the second prescribed medicine among the plurality of prescribed medicine. For example, when the regimen of the first prescribed medicine is to take twice a day, in the morning and evening, and the regimen of the second prescribed medicine is to take once a day, in the morning, it may be determined that the regimen of the first prescribed medicine is the same as a portion of the regimen of the second prescribed medicine.

For example, the electronic device may determine to package the first prescribed medicine together with a portion of the second prescribed medicine and package the remainder of the second prescribed medicine separately. As another example, the electronic device may determine to package the first prescribed medicine separately from the second prescribed medicine. In an embodiment, the electronic device may determine, based on a user input, whether to package the first prescribed medicine together with a portion of the second prescribed medicine.

In operation 320, when the electronic device determines not to package the first prescribed medicine and the second prescribed medicine together, the electronic device may display a guidance message for separate packaging of the first prescribed medicine and the second prescribed medicine through an output unit.

In operation 330, the electronic device may display a message regarding a medicine included in the prescription information. The electronic device may display a message regarding a medicine when there is a message mapped to the medicine included in the prescription information obtained based on the prescription. The electronic device may be used to reduce the burden on a pharmacist of having to remember precautionary information for individual medications by displaying messages mapped to medications based on prescription information.

For example, when a prescribed medicine is a medicine prohibited from being opened, the electronic device may display a guidance message through the output unit informing that the prescribed medicine may not be opened. When the prescribed medicine has a property of absorbing water and changing when exposed to air, the electronic device may display a message (e.g., "Medication prohibited from opening," "This medicine may not be opened," and the like) to prohibit the opening of the prescribed medicine.

For example, when a prescribed medicine has to be protected from light, a message (e.g., "This medication requires protection from light," "Please prepare a separate light-blocking envelope," "Please put in a light-blocking container," and the like) for protection from light may be displayed.

For example, the electronic device may display a warning message (e.g., "Female pharmacist prohibited from opening," "Cautionary medicine may cause birth defects", and the like) when a prescribed medicine is hazardous (e.g., a risk of giving birth to a deformed child when exposed).

Hereinafter, an example of a case where a plurality of prescribed medicines has a different number of days of medication is described.

Example 11: Function for Calculating the Total Quantity, where it is Displayed as Separate Packaging when the Total Number of Days of Medication is Different

TABLE 10

| Name of prescribed medicine | Single dose | Number of doses per day | Total number of days of medication | Total quantity |
|---|---|---|---|---|
| AAA 2 mg | 2 mg (1 tab) | 5 times/7 days → Mon thru Fri | 60 days (meaning 12 weeks) | 60 tab |
| AAA 5 mg | 2.5 mg (0.5 tab) | 5 times/7 days → Mon thru Fri | 60 days | 30 tab |
| AAA 2 mg | 4 mg (2 tab) | 2 times/7 days → Sat. Sun | 24 days | 48 tab |

In an embodiment, for a prescription prescribed by a general practitioner, prescription information obtained from the prescription may not include the total quantity of a medicine. Thus, the electronic device according to an embodiment may calculate the total quantity of the medicine by considering up to half (indicated as 0.5 tab in Table 10) of tablets included in a daily dosage.

The electronic device according to an embodiment may determine that a plurality of prescribed medicines included in the prescription information are to be given out in a plurality of packages (e.g., packaged in different pill pouch bags) based on the number of days of medication and/or regimen of the plurality of prescribed medicines included in the prescription information. For example, the electronic device may determine and/or display that at least one of the plurality of prescribed medicines is to be prepared separately when the plurality of prescribed medicines have a different number of days of medication and/or regimen and thus may not be packaged in a single pill pouch bag.

The electronic device according to an embodiment may determine that the prescribed medicine is to be given out in a plurality of packages based on the number of days of medication, when the number of days of medication of at least two prescribed medicines among the plurality of prescribed medicines of the prescription information is different from each other. For example, for the last medicine in Table 10, AAA 2 mg, the electronic device may determine and/or display that the last medicine is to be packaged and given out separately, in response to the total number of days of medication being different from the other medicines (e.g., the first medicine, AAA 2 mg, and the second medicine, AAA 5 mg).

Example 12: When Formulas are Calculated Separately for a Morning Medication when (1) Packaged all in Pill Pouch Bags and (2) Packaged in Individual Bottles

TABLE 11

| Name of prescribed medicine | Single dose | Number of doses per day | Total number of days of medication | Total quantity | Regimen |
|---|---|---|---|---|---|
| AAA 200 mg | 1 cap | 1 time | 182 days | 182 cap | Take once a day after breakfast |
| BBB 5 mg | 1 tab | 1 time | 182 days | 182 tab | Take once a day after breakfast |
| CCC 400 mg | 1 cap | 2 times | 182 days | 364 cap | Take twice a day after breakfast and dinner |
| DDD 300 mg | 1 cap | 2 times | 182 days | 364 cap | Take twice a day after breakfast and dinner |
| EEE 60 mg | 1 cap | 1 time | 182 days | 182 cap | Take once a day before bed |

When CCC 400 mg is included in the prescription information, the electronic device according to an embodiment may determine that CCC 400 mg is a medicine prohibited from opening, and display a notification (e.g., a message) indicating that CCC 400 mg is a medicine prohibited from opening. In addition, the electronic device may calculate the total quantity of CCC 400 mg as 364 capsules. Thereafter, the electronic device may determine the package count per packaging of CCC 400 mg. For example, a package of a first packaging type (e.g., bottle) of CCC 400 mg may contain 90 capsules, and a package of a second packaging type (e.g., plate) may contain 15 capsules. The electronic device may determine and/or display 4 packages of the first packaging type, 0 packages of the second packaging type, and 4 unit capsules for the giving out of 364 capsules of CCC 400 mg.

Example formula: $90 \times 4 + 4 = 364$

The regimen for the first prescribed medicine may be to take once a day, and the regimen for the second prescribed medicine may be to take twice a day. When the regimen for a medicine is to be taken once a day, there may be one formula to calculate the total quantity of the medicine. In a case where the regimen for a medicine is to be taken twice a day, for example, when there are packages of a first packaging (bottle: 100 tablets) and a second packaging (plate: 10 tablets) for DDD 300 mg in Table 11, the package count for each packaging may be determined in two approaches: (1) giving out both the medicine to be taken in the morning and the medicine to be taken in the evening in packages of a packaging type, and (2) giving out the medicine to be taken in the morning in pill pouch bags and giving out the medicine to be taken in the evening in packages of a packaging type. (1) When the medicine to be taken in the morning is packaged in pill pouch bags, the medicine to be taken in the evening is to be given out separately (e.g., in packages of a packaging type), so 182 tablets of the medicine to be taken in the evening may be prepared separately. (2) When both the medicine to be taken in the morning and the medicine to be taken in the evening are not packaged in pill pouch bags and are to be given out in packages of a package type (e.g. bottle, plate), the total quantity is 364 tablets so the medicine may be prepared according to formula $100 \times 3$ (bottles)$+10 \times 6$ (plates)$+4$ (tablets)=Total 364 (tablets).

Example 13: In a Case where all Morning Medicines are Packaged in Pill Pouch Bags and Only EEE Medicine is to be Taken in the Morning and Evening (Twice a Day), Deriving a Formula for when EEE to be Taken in the Evening is Separately Prepared

TABLE 12

| Name of prescribed medicine | Single dose | Number of doses per day | Total number of days of medication | Total quantity | Regimen |
|---|---|---|---|---|---|
| AAA 75 mg | 1 tab | 1 time | 126 days | 126 tab | Take once a day after breakfast |
| BBB 40/ 12.5 mg | 1 tab | 1 time | 126 days | 126 tab | Take once a day after breakfast |
| CCC 5 mg | 1 tab | 1 time | 126 days | 126 tab | Take once a day after breakfast |
| DDD 10/80 mg | 1 tab | 1 time | 126 days | 126 tab | Take once a day after breakfast |
| EEE 25 mg | 1 tab | 2 times | 126 days | 252 tab | Take twice a day after breakfast and dinner |
| FFF 0.6 mg sublingual tablet | 1 tab | 1 time | 5 days | 5 tab | Use under the tongue when needed |

As shown in Table 12, according to an embodiment, the regimen for the first prescribed medicine may be to take once a day after breakfast, and the regimen for the second prescribed medicine may be to take twice a day after breakfast and dinner. The electronic device according to an embodiment may package a medicine to be taken after breakfast in a pill pouch bag, and separately give out an evening dose of a medicine to be taken twice a day after breakfast and dinner. For example, in Table 12, when the regimen of a portion (e.g., AAA 75 mg, BBB 40/12.5 mg, CCC 5 mg, DDD 10/80 mg) of the medicines included in the prescription information is to take once a day in the morning and the regimen of another portion (e.g., EEE 25 mg) of the medicines included in the prescription information is to take twice a day in the morning and evening, the morning doses may be packaged together in pill pouch bags and the evening doses of the other portion (e.g., EEE 25 mg) may be packaged separately in another pill pouch bag.

Since all other medicines are to be taken once a day, there may be two formulas for
(1) when only EEE 25 mg evening doses are packaged separately and
(2) when both the morning and evening doses of EEE 25 mg and the other medicines are packaged together.

Figure 4:
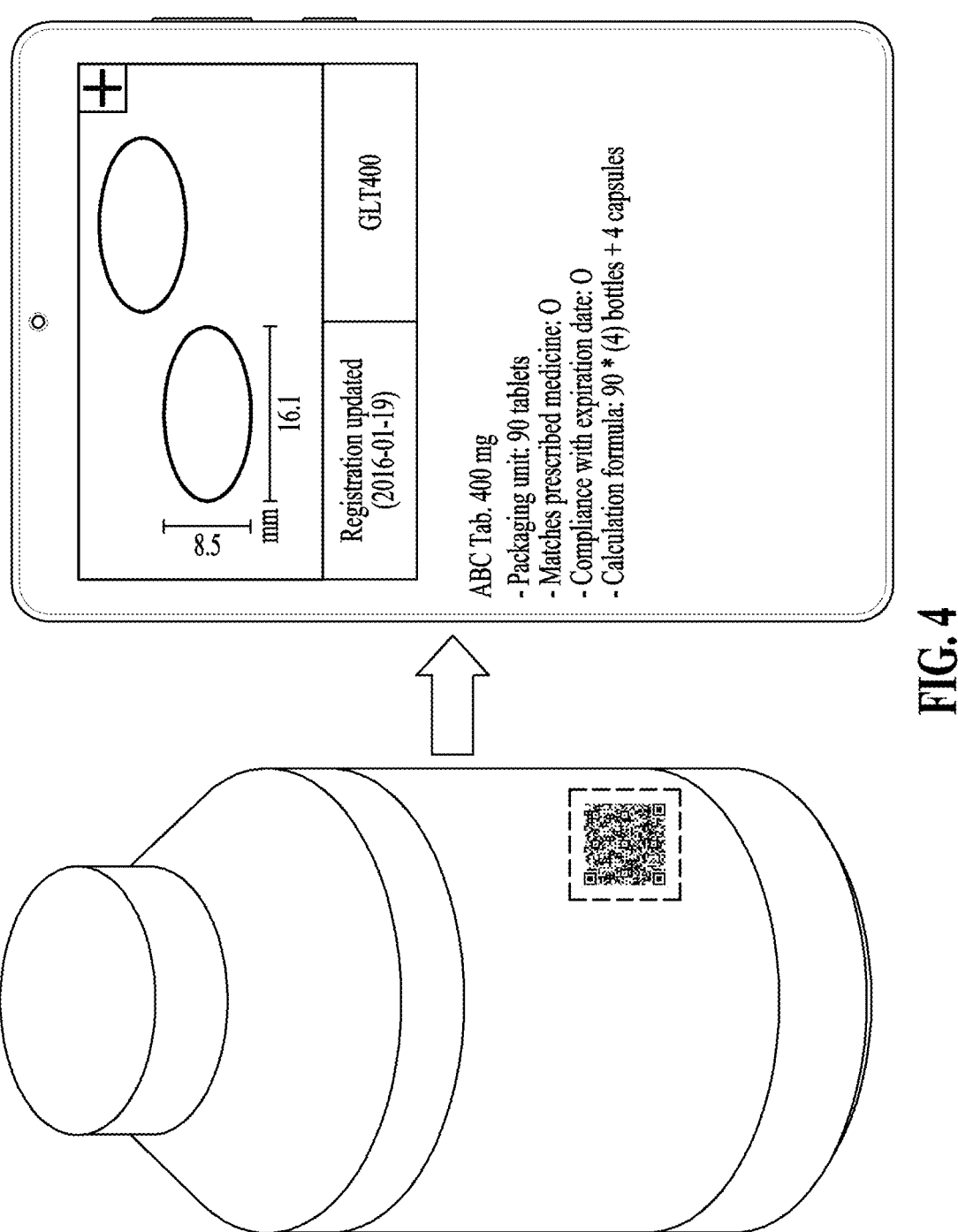
FIG. 4 illustrates an example of an interface for medicine identification in an electronic device according to various embodiments.

FIG. 4 illustrates an example of an interface for medicine identification in an electronic device according to various embodiments.

FIG. 4 is merely an example of a user interface design and may be modified according to the design.

A user (e.g., a pharmacist) may bring a target medicine to be given out. The user may capture a dosage form (e.g., tablet) of the target medicine and/or a packaging (e.g., bottle, box, or the like) of the target medicine. The electronic device may obtain an image corresponding to the dosage form of the target medicine and/or the packaging of the target medicine.

According to an embodiment, the user may capture a QR code included on the packaging of the target medicine using the electronic device. The electronic device may obtain an image corresponding to the QR code on the packaging of the target medicine.

For example, the QR code included on the packaging of the target medicine may include packaging type information related to at least one of a name, manufacturer, quantity, regimen, content of an active ingredient, or packaging type of the target medicine. The packaging type information is not limited to the at least one of the name, manufacturer, quantity, regimen, content of an active ingredient, or packaging type of the target medicine, and the packaging type information may also include other information related to the target medicine. As another example, the QR code included on the packaging of the target medicine may include a link accessible to information on the target medicine.

The electronic device according to an embodiment may display information on the target medicine and/or whether the target medicine may be given out, when the QR code included on the packaging of the target medicine is captured. For example, the electronic device may determine and/or display whether the target medicine may be given out based on whether the target medicine brought by the user matches a prescribed medicine. As another example, the electronic device may determine a limit on an expiration date of a prescribed medicine, and compare an expiration date of a target medicine with the determined limit on the expiration date of the prescribed medicine to determine and/or display whether the target medicine may be given out.

The determining and/or displaying of whether the target medicine may be given out based on prescription information and packaging type information is described in more detail below with reference to FIG. 5.

FIG. 5 is a flowchart illustrating an example of a preparation assistance method including an operation of determining and displaying whether a target medicine may be given out according to various embodiments.

In operation 510, an electronic device may obtain packaging type information corresponding to a packaging by capturing at least a portion of the packaging of a target medicine through an image capturer.

At least a portion of the packaging of the target medicine may include code information (e.g., a QR code or barcode). For example, the code information may be printed on at least a portion of an outer surface of the packaging. However, the example is not limited thereto, and at least a portion of the packaging of the target medicine may be, for example, an area in which information on the target medicine is stated. The electronic device may obtain the packaging type information by applying OCR to the area in which information on the target medicine is stated. The packaging type information may include at least one of a name, content of an active ingredient, dosage form, or packaging type of the target medicine.

In operation 520, the electronic device may determine whether the target medicine may be given out by verifying whether the target medicine is the same medicine as the prescribed medicine based on the packaging type information. The electronic device may determine that the target medicine may be given out, when the prescribed medicine is the same as the target medicine and the packaging of the target medicine is a packaging that is determined to be one or more of a plurality of available packaging of the prescribed medicine.

According to an embodiment, the electronic device may determine, based on the packaging type information and the prescription information, whether the name, content of the active ingredient, dosage form, and packaging type of the prescribed medicine match the name, content of the active ingredient, dosage form, and packaging type of the target medicine. The electronic device may determine that the target medicine may be given out when the name, content of the active ingredient, dosage form, and packaging type of the prescribed medicine each individually matches the name, content of the active ingredient, dosage form, and packaging type of the target medicine. A packaging of a prescribed medicine may be a packaging in which the package count is determined to be one or more among a plurality of available packaging of the prescribed medicine.

For example, the electronic device may determine that the prescribed medicine and the target medicine are the same medicine when the name, content of the active ingredient, and dosage form of the prescribed medicine are each individually identical to the name, content of the active ingredient, and dosage form of the target medicine. However, when the electronic device determines that the target medicine may be given out only because the prescribed medicine and the target medicine are the same, errors may occur due to the total quantity of the prescribed medicine and the complexity (e.g., a diversity of packaging units and packaging types) of the packaging as described above. Accordingly, the electronic device according to an embodiment may determine that the target medicine may be given out when the packaging of the target medicine is a packaging that is determined to be one or more of a plurality of available packaging of the prescribed medicine.

For example, for a total quantity of 360 tablets of a prescribed medicine AAA 1000 mg, the electronic device may determine 0 packages for a first packaging (e.g., 400 tablets) and 4 packages for a second packaging (e.g., 90 tablets). When the packaging of the target medicine AAA 1000 mg is the first packaging, even when the prescribed medicine and the target medicine are the same medicine, AAA 1000 mg, the electronic device may determine that the target medicine may not be given out because the package count of the first packaging of the prescribed medicine is determined to be "0." When the packaging of the target medicine AAA 1000 mg is the second packaging, the electronic device may determine that the target medicine may be given out because the prescribed medicine and the target medicine are the same medicine, AAA 1000 mg, and the package count of the second packaging of the prescribed medicine is determined to be 4.

According to an embodiment, the electronic device may determine whether the target medicine may be given out based on an expiration date of the target medicine. The electronic device may determine a limit on an expiration date of the prescribed medicine based on prescription date information, the total number of days of medication, and the grace period of the prescribed medicine among the prescription information. The electronic device may determine that a target medicine may be given out when the expiration date of the target medicine included in the packaging type information is later than the limit on the expiration date of the prescribed medicine. The electronic device may determine that the target medicine may not be given out when the expiration date of the target medicine included in the packaging type information precedes the limit on the expiration date of the prescribed medicine.

In operation 530, the electronic device may display, through an output unit, whether the target medicine may be given out.

In an embodiment, the electronic device may determine and/or display whether a target medicine may be given out or not based on at least a portion (e.g., a QR code) of a packaging of the target medicine. For example, when the target medicine may be given out, the electronic device may display a first graphical representation (e.g., an "O"), and when the target medicine may not be given out, the electronic device may display a second graphical representation (e.g., an "X").

In addition, when a medicine is not given out as it is (e.g., in a packaging of a packaging type) and prepared by an automatic tablet counting and dispensing (ATC) machine and packaged in a pill pouch bag, medicine contained in the machine may be packaged accurately by computer, but for medicine not contained in the machine, a pharmacist may have to bring the medicine bottle and add the medicine to the ATC machine. When the medicine bottle is brought and the medicine is put into the machine, the electronic device may capture a QR code on the medicine bottle before the medicine is put into the ATC machine to determine and/or display whether the medicine brought matches prescription information (or may be given out).

For example, the electronic device may prevent and/or reduce the mistake of putting AAA 5/160 mg in an ATC machine instead of AAA 5/80 mg when AAA 5/160 mg is brought by mistake. The electronic device may prevent and/or reduce confusion between AAA 5 mg and AAA' 5 mg, which have very similar medicine names (e.g., prevent and/or reduce confusion between AAA tablets and AAA Plus tablets, or between AAA tablets and AAA XQ tablets).

A user (e.g., a pharmacist) may avoid and/or reduce confusion between a prescribed medicine (e.g., AAA) and a medicine with a different name (e.g., AAA Plus), the content (e.g., BBB 500 mg) of an active ingredient of a prescribed medicine and the content (e.g., BBB 1000 mg) of a different active ingredient, and/or a packaging (e.g., a CCC bottle containing CCC 50 tablets) of a prescribed medicine and a different packaging (e.g., a CCC bottle containing CCC 100 tablets) by being provided with whether a target medicine may be given out based on the electronic device. In addition, the user (e.g., the pharmacist) may prevent and/or reduce a medicine with an expiration date earlier than a time at which a patient is expected to take the medicine, considering the number of days of medication and/or a grace period, from being given out, by receiving a result of comparing the expiration date of the target drug with the expiration date of the prescribed drug based on the electronic device.

In an embodiment, the electronic device may display a graphical representation of an order relation between a limit on an expiration date of a prescribed medicine and an expiration date of a target medicine. For example, the electronic device may display a circle (e.g., an "O") when the expiration date of the target medicine is later than the limit on the expiration date of the prescribed medicine. The electronic device may display an X (e.g., "X") when the expiration date of the target medicine is before the limit on the expiration date of the prescribed medicine. The electronic device according to an embodiment may help prevent and/or reduce prescriptions for medications with inappropriate expiration dates from being dispensed.

In operation 540, the electronic device may obtain an image of the target medicine when the target medicine is to be given out.

For example, the electronic device may obtain an image of the target medicine packaged in a pill pouch bag through the image capturer when the target medicine is packaged in a pill pouch bag.

As another example, when a user input instructing the target medicine to be given out is obtained, an image of a scene where the target medicine is delivered to the patient may be obtained through the image capturer.

The electronic device according to an embodiment may capture an image of a medicine to be given out. The image may include at least one of an image taken of at least a portion of the medicine to be given out or an image taken of the entire medicine. An image stored in the electronic device may be used as evidence of the type and total number of medicines that have been given out. The image may be taken of a scene where the medicine is delivered to the patient. The image may be taken of a scene where the patient pays for the medicine. According to an embodiment, the image may include a single frame image (e.g., a still image) or a plurality of frame images (e.g., a video).

The electronic device may obtain evidence that the medicine matching prescription information has been delivered to the patient through the captured image. For example, an image captured by the electronic device may be used to verify that a medicine is accurately delivered to a patient, and may be used as evidence to address complaints from patients that they received insufficient medication, did not receive a portion of the medication at all, or have already paid for the medication.

In a conventional pharmacy system, CCTVs may be widely used, but they may be difficult to use as evidence because a pharmacist may cover the screen. Also, it may take a lot of time to review CCTV footage, but by finding the evidence in a short period of time, time and effort may be reduced. The electronic device according to an embodiment may also replace pharmacy insurance (e.g., 100,000 won per month). The electronic device may capture an image that may be used as evidence when a patient claims they did not receive the medication. In the case of a pharmacy CCTV, a storage period may be about 2 months, where all information is deleted after 2 months, but the image captured by the electronic device may be permanently stored in a cloud and used as evidence. For reference, pharmacists may often be involved in disputes over dispensing, so the pharmacists may be covered by insurance.

Hereinafter, an example of a case where a target medicine is determined to be given out according to an expiration date of the target medicine based on a limit on the expiration date of a prescribed medicine is described.

Example 14: Determining Whether a Target Medicine May be Given Out Based on the Limit on the Expiration Date

TABLE 13

| Name of prescribed medicine | Single dose | Number of doses per day | Total number of days of medication | Total quantity | Regimen |
|---|---|---|---|---|---|
| AAA 75 mg | 1 tab | 1 time | 126 days | 126tab | Take once a day after breakfast |

29

TABLE 13-continued

| Name of prescribed medicine | Single dose | Number of doses per day | Total number of days of medication | Total quantity | Regimen |
|---|---|---|---|---|---|
| BBB 40/ 12.5 mg | 1 tab | 1 time | 126 days | 126 tab | Take once a day after breakfast |
| CCC 5 mg | 1 tab | 1 time | 126 days | 126 tab | Take once a day after breakfast |
| DDD 10/80 mg | 1 tab | 1 time | 126 days | 126 tab | Take once a day after breakfast |
| EEE 25 mg | 1 tab | 2 times | 126 days | 252 tab | Take twice a day after breakfast and dinner |
| FFF 0.6 mg sublingual tablet | 1 tab | 1 time | 5 days | 5 tab | Use under the tongue when needed |

The electronic device may calculate a limit on an expiration date based on the number of days of medication of prescription information, which is 126 days (e.g., 4 months), and display the limit on the expiration date. The electronic device may calculate the limit on the expiration date considering a medication period from a current date (e.g., a prescription date), and display the calculated limit on the expiration date. The medication period may include a period considering the number of days of medication (e.g., 4 months) as well as a grace period (e.g., 3 months).

Due to the nature of medicine, there may be a possibility of complaints when the medicine is prepared to match the expiration date, and depending on the compliance with the medicine of the patient, the medicine may be taken for a longer period than the number of days of medication. Therefore, a medication period based on the number of days of medication and grace period may be considered. When the electronic device captures a QR code on a medicine bottle, the electronic device may compare the expiration date of the medicine with the limit on the expiration date based on the calculated limit on the expiration date. The electronic device may determine and/or display whether the expiration date of the medicine has exceeded the calculated limit on the expiration date. For example, when a pharmacist brings a medicine and captures the QR code on the medicine bottle with the electronic device, the electronic device may determine and display whether the expiration date of the medicine is after (e.g., indicated by an "O") the limit on the expiration date or whether the expiration date of the medicine is before (e.g., indicated by an "X") the limit on the expiration date.

FIGS. 6A to 6F illustrate various packaging of medicines according to various embodiments.

As mentioned above, a pharmacist may capture a prescription (or a QR code on the prescription) with an electronic device. The electronic device may obtain prescription information when the prescription is captured. The electronic device may determine and/or display the total quantity of a medicine and the package count per packaging of the medicine based on the prescription information.

The pharmacist may bring a medicine to be given out by referring to the total quantity of the medicine and/or the package count per packaging of the medicine displayed on the electronic device. The pharmacist may capture a medicine bottle (or a QR code on the medicine bottle) of the medicine to be given out with the electronic device. When the medicine bottle is captured, the electronic device may determine and/or display information on at least one of a name of the medicine, content of an active ingredient of the medicine, packaging type, or an expiration date of the medicine. For example, the electronic device may determine and/or display whether the name and content of the active ingredient of the medicine match the prescription information. The electronic device may determine and/or display the number (also referred to herein as a "packaging unit") of dosage forms (e.g., unit tablets) contained in the medicine bottle. The electronic device may determine and/or display an order relation between an expiration date of the medicine in the medicine bottle and a limit on the expiration date.

In a conventional pharmacy system, the pharmacist may visually check whether a medicine he or she has brought matches a medicine in the prescription and deliver the medicine to a patient. No matter how carefully the pharmacist may check, the pharmacist may make a mistake. For example, in the case of AAA medicine, the content of the active ingredient of the medicine may vary greatly, such as 10 mg, 20 mg, and 40 mg, and in the case of BBB medicine, the content of the active ingredient of the medicine may vary, such as 5/80 mg, 5/160 mg, 10/80 mg, and 10/160 mg. In addition, there may be a CCC' (e.g., CCC Plus Pro, CCC", CCC XQ, and the like) that is distinct from CCC. Since there are various types of medicines, mistakes by the pharmacist may easily occur.

In an embodiment, the electronic device may determine, when a QR code of a medicine bottle is captured, whether the medicine in the prescription and the medicine (e.g., the medicine in the medicine bottle) brought by the pharmacist are of the same type, and display a circle (e.g., "O") when the medicines are of the same type, and display an X (e.g., "X") when the medicines are of different types. When a mistake occurs (e.g., when the medicine in the prescription is a different type than the medicine in the medicine bottle), the electronic device may provide an interface that guides the pharmacist to bring the medicine back.

Figure 6A:
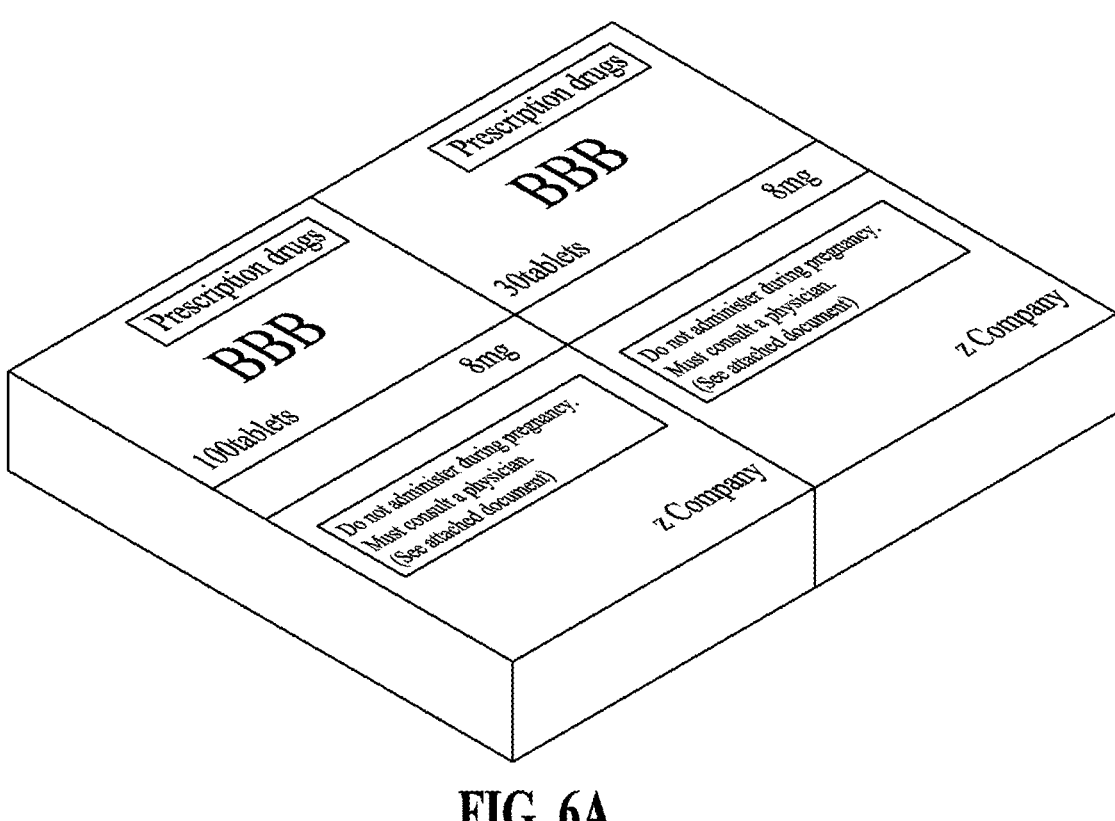
FIGS. 6A to 6F illustrate various packaging of medicines according to various embodiments.
Figure 6B:
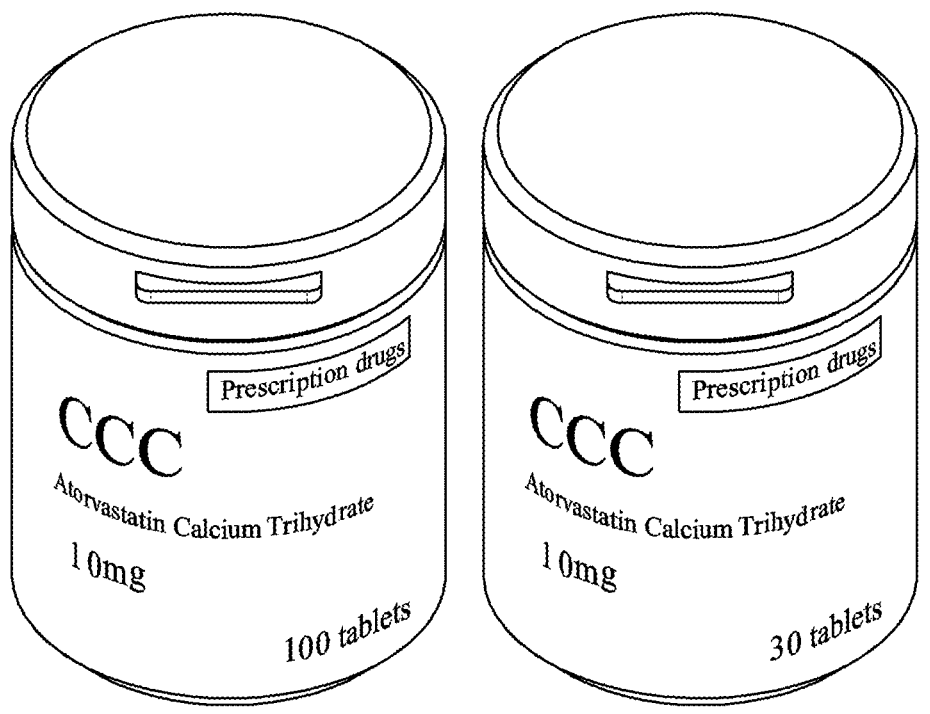

As shown in FIG. 6A, in the case of BBB, the size and/or shape of the packaging of a packaging type containing 100 tablets and a packaging type containing 30 tablets may be the same or similar. As shown in FIG. 6B, in the case of CCC for example, the size and/or shape of the packaging of a packaging type containing 100 tablets and a packaging type containing 30 tablets may be the same or similar.

The electronic device according to an embodiment may determine and/or display a packaging type of a medicine bottle when a QR code of the medicine bottle is captured. For example, the electronic device may display whether the medicine bottle contains 30 tablets or 100 tablets when the QR code of the medicine bottle is captured. (For example, when the shape and size of the BBB 30-tablet bottle and the BBB 100-tablet bottle are the same, and 90 BBB tablets are to be given out, a case where 3 bottles of 100 BBB tablets being mistakenly given out instead of 3 bottles of 30 BBB tablets may be avoided and/or reduced.)

A pharmacist may make the mistake of missing an expiration date of a medicine while checking the content of an active ingredient. The electronic device according to an embodiment may verify the content of an active ingredient of a medicine, the expiration date of the medicine, and the packaging type of the medicine all at once.

Figure 6C:
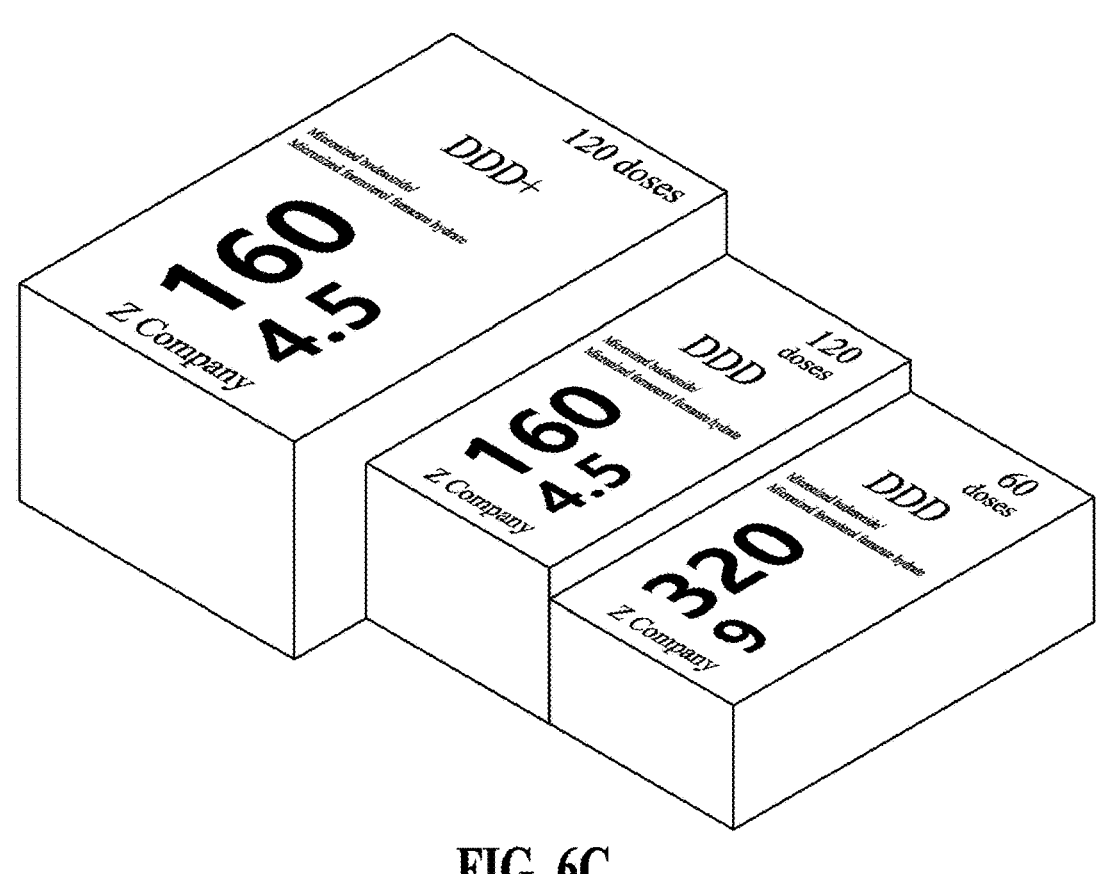

FIG. 6C is a diagram illustrating a plurality of different medicines having similar packaging.

Referring to FIG. 6C, DDD and DDD+ may be confused by a pharmacist due to the similarity in packaging, and in particular, DDD+ may have various active ingredient contents.

For example, in the case of an inhalant, there may be a DDD and DDD+, which have the same ingredients but different inhalation manner. In the case of an inhalant of DDD+, the inhalant may have a first active ingredient content (e.g., 160/4.5 μg) and a second active ingredient content (e.g., 80/2.25 μg), and in the case of an inhalant of DDD, the inhalant may have a third active ingredient content (e.g., 160/4.5 μg). DDD may have different packaging for refills and main machine use. For example, there may be separate packaging for 60 doses and 120 doses.

The electronic device may prevent and/or reduce mistakes related to medicine having similar packaging or a plurality of active ingredient contents by determining and/or displaying whether the medicine brought by the pharmacist matches the prescription information when the QR code on the medicine bottle is captured.

Figure 6D:
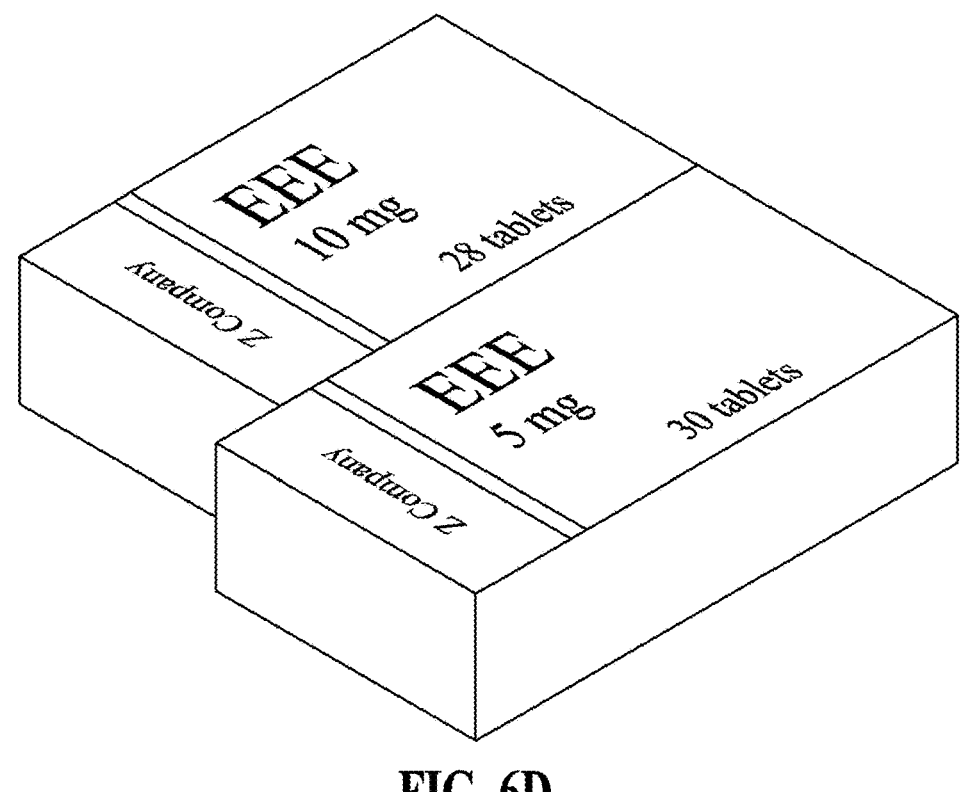

FIG. 6D is a diagram illustrating an example of a medicine of which a packaging varies depending on the content of an active ingredient.

The packaging of a medicine may be confusing to a pharmacist. For example, a first packaging of EEE 5 mg may contain 30 tablets, and a second packaging of EEE 10 mg may contain 28 tablets.

Since the packaging units of medicines with the same ingredients and different contents are different, the pharmacist may confuse the quantity of the medicines to be given out. In this case, a formula for giving out the medicine may be provided to help prevent and/or reduce confusion of pharmacists.

TABLE 14

| Name of prescribed medicine | Single dose | Number of doses per day | Total number of days of medication | Total quantity | Regimen |
|---|---|---|---|---|---|
| FFF eye drops | 1 | 1 | 1 | | |

Figure 6E:
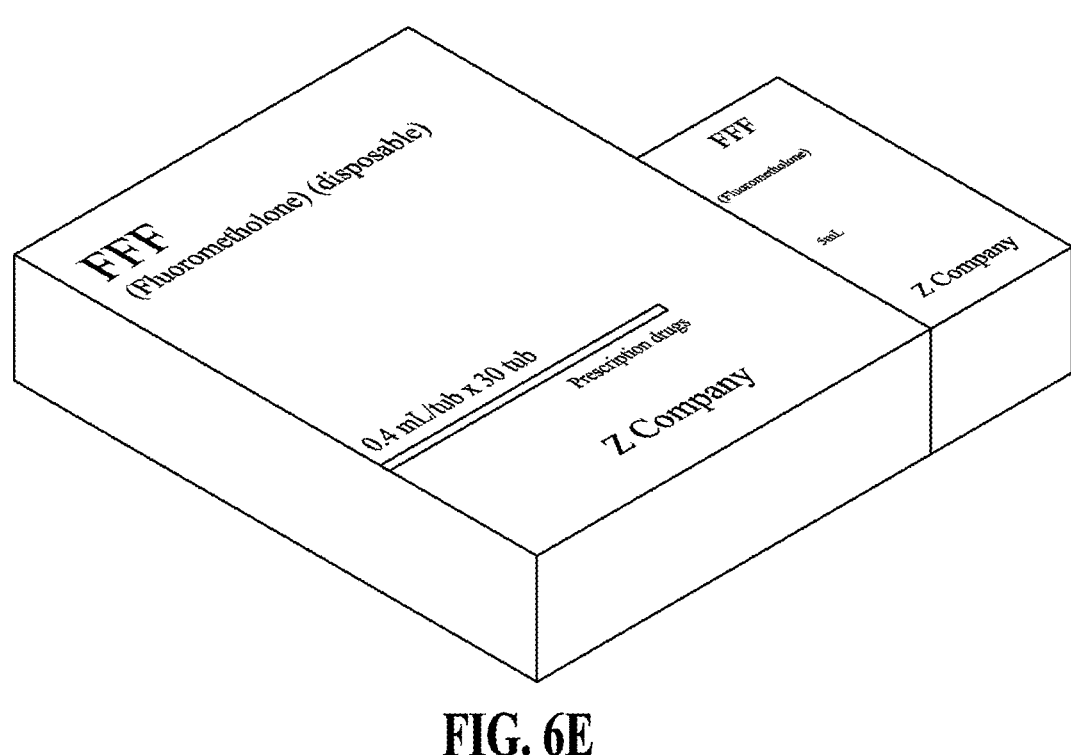

FIG. 6E is a diagram illustrating an example of a medicine packaged in a plurality of packaging types.

In the case of FFF eye drops, there may be a first packaging type containing 30 individually packaged disposable tubes and a second packaging type containing 5 mL of an active ingredient which is reusable.

In the case of the FFF eye drops, since the single dose, number of doses per day, and total number of days of medication are all "1" on the prescription, a pharmacist who does not know that the FFF eye drops are available in two types of packaging may be more likely to make the mistake of preparing the wrong medicine without checking a code number. In an embodiment, the electronic device may prevent and/or reduce a mistake by determining and/or displaying whether a medicine in a corresponding medicine bottle matches prescription information (or whether the medicine in the corresponding medicine bottle may be given out) when a QR code of the medicine bottle is captured.

Figure 6F:
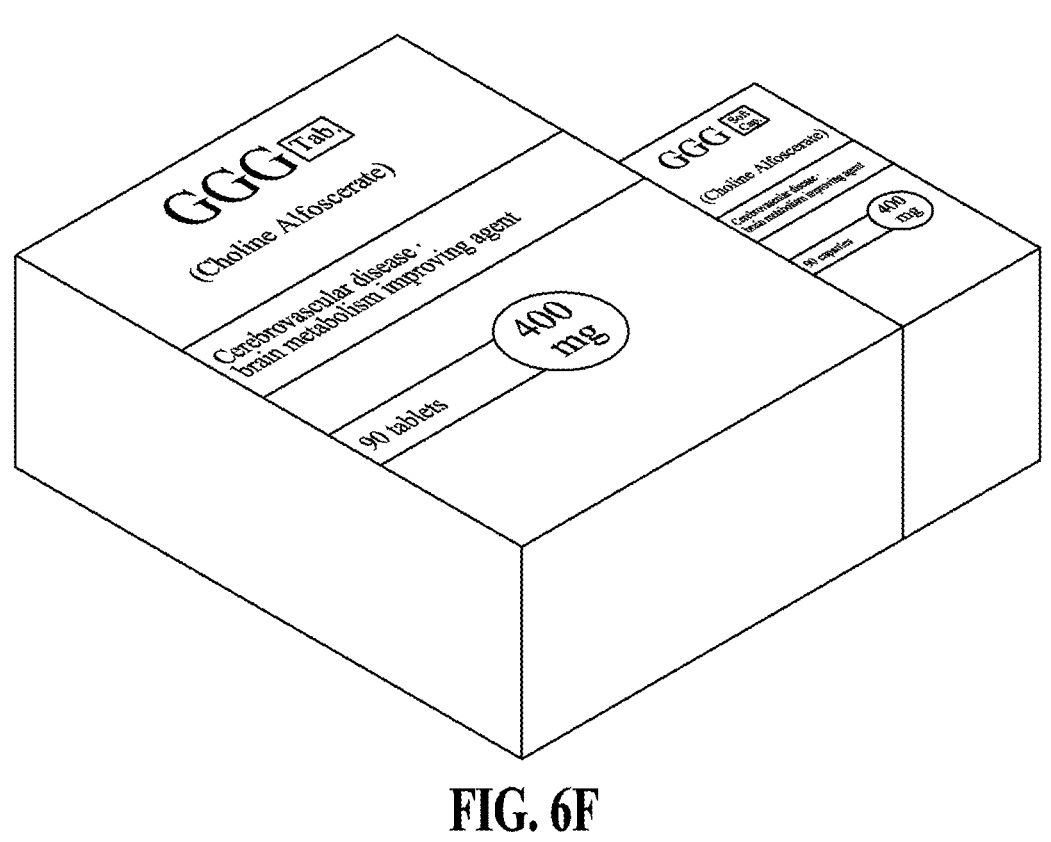

FIG. 6F is a diagram illustrating an example of a medicine having the same active ingredient and same content of the active ingredient with different dosage forms.

In the case of GGG, there may be GGG tablets in tablet form and GGG capsules in capsule form.

FIG. 7 is a flowchart illustrating an example of a preparation assistance method including an operation of managing an inventory database based on medicines brought in from a wholesaler and medicines given out to patients according to various embodiments.

In operation 710, the electronic device may obtain order information on a medicine to be brought in from a wholesaler to a pharmacy.

The order information may include at least one of a name, the content of an active ingredient, packaging type, dosage form, or the number (e.g., the order quantity) of packages per packaging of an ordered medicine requested by the pharmacy. In an embodiment, the electronic device may obtain the order information based on a user input. In an embodiment, the electronic device may obtain the order information by capturing at least a portion of an order form. At least a portion of the order form may include a QR code (or barcode). At least a portion of the order form may be an area containing order details, and the electronic device may obtain the order information by applying OCR to the at least a portion of the order form.

In operation 720, the electronic device may obtain information on the medicine brought in by capturing at least a portion of a packaging of the medicine brought in through an image capturer.

The electronic device according to an embodiment may determine the information on the medicine brought in when the medicine is brought in from the wholesaler to the pharmacy. The information on the medicine brought in may include at least one of a name of the medicine, the content of an active ingredient of the medicine, a dosage form, packaging type, quantity (e.g., order quantity), the wholesaler who provided the medicine, or an expiration date. For example, the electronic device may obtain the information on the medicine brought in through OCR and/or a QR code.

In operation 730, the electronic device may determine whether the medicine brought in matches the order information based on the obtained order information and information on the medicine brought in.

The electronic device according to an embodiment may determine whether a medicine brought in from a wholesaler to a pharmacy matches order information. For example, the electronic device may determine whether the medicine brought in from the wholesaler is the same (e.g., the name, content of an active ingredient, and/or packaging type of the medicine are the same) as an ordered medicine in the order information, and whether an ordered quantity is the same as the quantity of medicine brought in. For example, the electronic device may capture the medicine (or a QR code attached to a packaging of the medicine) brought in from the wholesaler to the pharmacy. The electronic device may determine whether the quantity of the medicine matches the order quantity in the order information based on an image obtained by capturing the medicine brought in.

In operation 740, the electronic device may update an inventory database based on the information on the medicine brought in when the medicine brought in matches the order information.

The electronic device may change (e.g., update) the inventory management database to manage the inventory of medicines based on the information on the medicine brought in. For example, the electronic device may determine and display an inventory quantity of a medicine by linking and inputting the quantity of the medicine brought in, into a pharmacy program.

In operation 750, when the electronic device obtains a request to return a medicine brought in from a user, the electronic device may display information on the wholesaler that supplied the medicine brought in.

When the medicine is brought in to the pharmacy from a plurality of wholesalers, the pharmacist may be confused as to which wholesaler the medicine came from. In this case, according to an embodiment, the electronic device may identify the wholesaler that supplied the medicine from among the plurality of wholesalers. As a result, the electronic device according to an embodiment may determine the wholesaler that supplied the medicine when the pharmacist returns the medicine.

In a transaction statement received from the wholesaler, information such as a code number, the content of an active ingredient such as 30T, and the quantity of a medicine may all be included. By capturing the transaction statement received from the wholesaler and linking and inputting the captured transaction statement to the pharmacy program, the inventory quantity and the wholesaler from which the medicine came may be identified, thereby making it easier to return the medicine.

In operation 760, the electronic device may receive a user input instructing whether to give out a target medicine from the user. The electronic device may update the inventory database when the user input instructs the target medicine to be given out.

The electronic device according to an embodiment may perform an automatic ordering function based on the inventory database. For example, the electronic device may display an order notification message for a packaging type of a medicine when an inventory quantity of the corresponding packaging type of the medicine in the inventory database is less than or equal to a recommended inventory quantity of the corresponding packaging type of the medicine. However, the present disclosure is not limited to the example of displaying an order notification message. For example, the electronic device may automatically order a packaging type of a medicine when the inventory quantity of the corresponding packaging type of the medicine in the inventory database is less than or equal to the recommended inventory quantity of the corresponding packaging type of the medicine.

Figure 8:
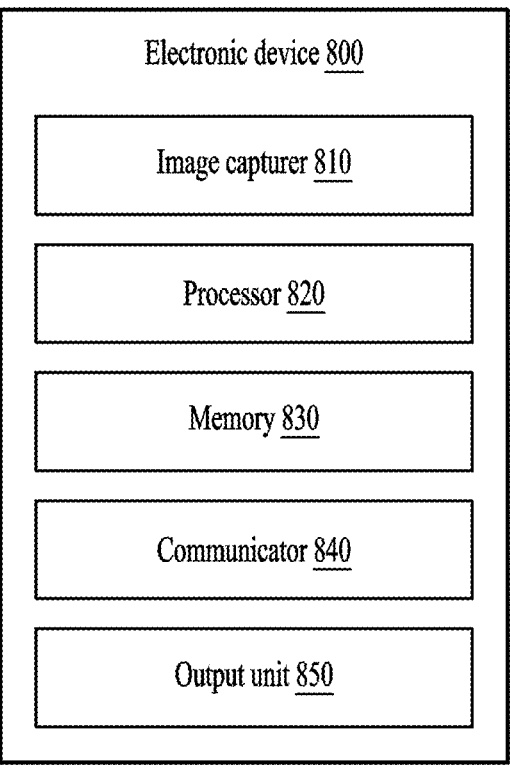
FIG. 8 is a block diagram illustrating an exemplary configuration of an electronic device according to various embodiments.

FIG. 8 is a block diagram illustrating an exemplary configuration of an electronic device according to various embodiments.

An electronic device 800 according to an embodiment may include an image capturer 810, a processor 820, a memory 830, a communicator 840, and an output unit 850.

The image capturer 810 may capture at least a portion of a prescription, a target medicine brought by a user, an order form, and/or a medicine brought in from a wholesaler.

The processor 820 may determine the total quantity of a prescribed medicine, the package counts of a plurality of available packaging of the prescribed medicine, and/or a limit on an expiration date of the prescribed medicine based on prescription information obtained from a prescription. The processor 820 may determine whether a target medicine may be given out by comparing the prescription information obtained from the prescription and information on the target medicine.

The processor 820 may determine whether a medicine brought in matches order information based on the order information and information on the medicine brought in. When the processor 820 obtains a request to return a medicine brought in, the processor 820 may determine information on a wholesaler that supplied the medicine brought in.

The processor 820 may manage an inventory database. When the processor 820 obtains a user input instructing a target medicine to be given out, the processor 820 may update an inventory of the target medicine in the inventory database. The processor 820 may update the inventory of the medicine brought in in the inventory database when the medicine brought in matches the order information.

The memory 830 may temporarily and/or permanently store instructions for an operation of the processor 820.

The communicator 840 may establish wired and/or wireless communications with an external device (e.g., an inventory database, a database of the Korea Pharmaceutical Information Center).

The output unit 850 may provide information obtained by the processor 820 to a user by outputting the information. The output unit 850 may include a speaker and/or an output unit. For example, the output unit 850 may display prescription information, a plurality of package counts for a plurality of packaging, a limit on an expiration date, whether a target medicine may be given out, order information, and/or whether a medicine brought in matches the order information.

The embodiments described herein may be implemented using a hardware component, a software component and/or a combination thereof. A processing device may be implemented using one or more general-purpose or special-purpose computers, such as, for example, a processor, a controller and an arithmetic logic unit (ALU), a digital signal processor (DSP), a microcomputer, a field-programmable gate array (FPGA), a programmable logic unit (PLU), a microprocessor, or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is singular; however, one of ordinary skill in the art will appreciate that a processing device may include a plurality of processing elements and a plurality of types of processing elements. For example, the processing device may include a plurality of processors, or a single processor and a single controller. In addition, different processing configurations are possible, such as parallel processors.

The software may include a computer program, a piece of code, an instruction, or some combination thereof, to independently or uniformly instruct or configure the processing device to operate as desired. Software and data may be embodied permanently or temporarily in any type of machine, component, physical or virtual equipment, or computer storage medium or device capable of providing instructions or data to or being interpreted by the processing device. The software also may be distributed over network-coupled computer systems so that the software is stored and executed in a distributed fashion. The software and data may be stored by one or more non-transitory computer-readable recording mediums.

The methods according to the above-described embodiments may be recorded in non-transitory computer-readable media including program instructions to implement various operations of the above-described embodiments. The media may also include, alone or in combination with the program instructions, data files, data structures, and the like. The program instructions recorded on the media may be those specially designed and constructed for the purposes of embodiments, or they may be of the kind well-known and available to those having skill in the computer software arts.

Examples of non-transitory computer-readable media include magnetic media such as hard disks, floppy disks, and magnetic tape; optical media such as CD-ROM discs and/or DVDs; magneto-optical media such as optical discs; and hardware devices that are specially configured to store and perform program instructions, such as read-only memory (ROM), RAM, flash memory, and the like. Examples of program instructions include both machine code, such as produced by a compiler, and files containing higher-level code that may be executed by the computer using an interpreter.

The above-described hardware devices may be configured to act as one or more software modules in order to perform the operations of the above-described embodiments, or vice versa.

As used herein, "A or B," "at least one of A and B," "at least one of A or B," "A, B or C," "at least one of A, B and C," and "at least one of A, B, or C," each of which may include any one of the items listed together in the corresponding one of the phrases, or all possible combinations thereof.

As described above, although the examples have been described with reference to the limited drawings, a person skilled in the art may apply various technical modifications and variations based thereon. For example, suitable results may be achieved if the described techniques are performed in a different order, and/or if components in a described system, architecture, device, or circuit are combined in a different manner, and/or replaced or supplemented by other components or their equivalents.

Although the best mode contemplated by the inventors of carrying out the present invention is disclosed above, practice of the above invention is not limited thereto. It will be manifest that various additions, modifications and rearrangements of the features of the present invention may be made without deviating from the spirit and the scope of the underlying inventive concept.

Accordingly, other implementations are within the scope of the following claims.

The invention claimed is:

1. A preparation assistance method performed by an electronic device, the method comprising:
obtaining prescription information corresponding to a prescription, based on an image obtained by capturing at least a portion of the prescription through an image capturer;
determining a total quantity of a prescribed medicine based on the obtained prescription information;
determining package counts of a plurality of available packaging types of the prescribed medicine, based on the determined total quantity of the prescribed medicine;
displaying the determined package counts through an output unit;
determining whether to package a first prescribed medicine and a second prescribed medicine together based on at least one of the number of days of medication or regimen of each of the first prescribed medicine and the second prescribed medicine, based on the prescription information;
in response to it being determined that the first prescribed medicine and the second prescribed medicine are not to be packaged together, displaying a guidance message for separate packaging of the first prescribed medicine and the second prescribed medicine through the output unit;

further displaying a content of an active ingredient of the prescribed medicine together with a name of the prescribed medicine through the output unit, in response to the content of the active ingredient of the prescribed medicine not being stated in the prescription;
wherein the determining of the package counts of the plurality of packaging types comprises:
determining a first quantity combination comprising the package counts of the plurality of packaging types for the total quantity of the prescribed medicine; and
determining a second quantity combination in which the package count of at least one packaging type is different from the first quantity combination, for the total quantity of the prescribed medicine; and
training a neural network to determine a count of objects in a captured image.

2. The method of claim 1, wherein
the obtaining of the prescription information comprises:
obtaining in-hospital prescription information within a hospital; and
skipping the obtaining of the prescription information through the image capturer, based on obtaining the in-hospital prescription information.

3. The method of claim 1, wherein
the determining of the total quantity of the prescribed medicine comprises:
determining a daily dosage of the prescribed medicine by adding up single doses for each time of administration, in response to the number of doses per day of the prescribed medicine being two or more and the single doses of the prescribed medicine being different depending on the time of administration; and
calculating the total quantity of the prescribed medicine by multiplying the total number of days of medication of the prescribed medicine by the determined daily dosage.

4. The method of claim 1, wherein
the determining of the package counts of the plurality of packaging types comprises:
determining the package counts of a plurality of available packaging types for each of the prescribed medicine, in response to the prescription information comprising a plurality of prescribed medicines.

5. The method of claim 1, further comprising:
obtaining packaging type information corresponding to a packaging by capturing at least a portion of the packaging of a target medicine through the image capturer;
determining whether the target medicine may be given out by verifying whether the target medicine is the same medicine as the prescribed medicine, based on the packaging type information; and
displaying whether the target medicine may be given out through the output unit.

6. The method of claim 5, wherein
the determining of whether the target medicine may be given out comprises:
determining a limit on an expiration date of the prescribed medicine, based on prescription date information, the total number of days of medication, and a grace period of the prescribed medicine among the prescription information;
determining that the target medicine may be given out, in response to an expiration date of the target medicine included in the packaging type information being later than the limit on the expiration date of the prescribed medicine; and determining that the target medicine may not be given out, in response to the expiration date of the target medicine included in the packaging type information being earlier than the limit on the expiration date of the prescribed medicine.

7. The method of claim 5, further comprising:
obtaining an image of a scene where the target medicine is delivered to a patient through the image capturer, in response to a user input instructing the target medicine to be given out.

8. The method of claim 1, further comprising:
obtaining order information on a medicine to be brought in from a wholesaler to a pharmacy;
obtaining information on the medicine brought in by capturing at least a portion of a packaging of the medicine brought in through the image capturer;
determining whether the medicine brought in matches the order information, based on the obtained order information and the information on the medicine brought in; and
updating an inventory database based on the information on the medicine brought in, in response to the medicine brought in matching the order information.

9. The method of claim 8, further comprising:
displaying information on the wholesaler that supplied the medicine brought in, in response to obtaining a request to return the medicine brought in from a user.

10. The method of claim 8, further comprising:
receiving a user input instructing whether to give out a target medicine from a user, and
updating the inventory database, in response to the user input instructing the target medicine to be given out.

11. A non-transitory computer-readable storage medium storing instructions that, when executed by a processor, cause the processor to perform the method comprising the steps of;
obtaining prescription information corresponding to a prescription based on an image obtained by capturing at least a portion of the prescription through an image capturer;
determining a total quantity of a prescribed medicine based on the obtained prescription information;
determine package counts of a plurality of available packaging types of the prescribed medicine, based on the determined total quantity of the prescribed medicine;
displaying the determined package counts through an output unit;
determining whether to package a first prescribed medicine and a second prescribed medicine together based on at least one of the number of days of medication or regimen of each of the fast prescored medicine and the second prescribed medicine, based on the prescription information; and
in response to it being determined that the first prescribed medicine and the second prescribed medicine are not to be packaged together, displaying a guidance message for separate packaging of the first prescribed medicine and the second prescribed medicine through the output unit;
further displaying a content of an active ingredient of the prescribed medicine together with a name of the prescribed medicine through the output unit, in response to the content of the active ingredient of the presented medicine not being stated in the prescription;
wherein the determining of the package counts of the plurality of packaging types comprises
determining a first quantity combination comprising the package counts of the plurality of packaging types for the total quantity of the prescribed medicine; and
determining a second quantity combination in which the package count of at least one packaging type is different from the first quantity combination, for the total quantity of the prescribed medicine; and
training a neural network to determine a count of objects in a captured image.

12. An electronic device, comprising:
an image capturer configured to capture at least a portion of a prescription;
a processor configured to obtain prescription information corresponding to the prescription based on an image obtained by capturing at least a portion of the prescription through the image capturer, determine a total quantity of a prescribed medicine based on the obtained prescription information, and determine the package counts of a plurality of available packaging types of the prescribed medicine based on the determined total quantity of the prescribed medicine; and
an output unit configured to display the determined package counts,
wherein the processor further configured to:
determine whether to package a first prescribed medicine and a second prescribed medicine together based on at least one of the number of days of medication or regimen of each of the first prescribed medicine and the second prescribed medicine, based on the prescription information,
in response to it being determined that the first prescribed medicine and the second prescribed medicine are not to be packaged together, display a guidance message for separate packaging of the first prescribed medicine and the second prescribed medicine through the output unit,
further display a content of an active ingredient of the prescribed medicine together with a name of the prescribed medicine through the output unit, in response to the content of the active ingredient of the prescribed medicine not being stated in the prescription;
wherein the determined package counts of the plurality of packaging types includes:
a first quantity combination comprising the package counts of the plurality of packaging types for the total quantity of the prescribed medicine; and
a second quantity combination in which the package count of at least one packaging type is different from the first quantity combination, for the total quantity of the prescribed medicine; and
training a neural network to determine a count of objects in a captured image.

* * * * *